United States Patent
Palmer et al.

(10) Patent No.: US 9,398,944 B2
(45) Date of Patent: Jul. 26, 2016

(54) LOCK BAR SPRING AND CLIP FOR IMPLANT DEPLOYMENT DEVICE

(71) Applicant: Covidien LP, Mansfield, MA (US)

(72) Inventors: Mitchell Palmer, Wake Forest, NC (US); Jason T. Iceman, Cheshire, CT (US); Ofek Levin, Moshav Amirim (IL); Arie Levy, Ramat-Gan (IL)

(73) Assignee: COVIDIEN LP, Mansfield, MA (US)

( * ) Notice: Subject to any disclaimer, the term of this patent is extended or adjusted under 35 U.S.C. 154(b) by 205 days.

(21) Appl. No.: 13/720,141

(22) Filed: Dec. 19, 2012

(65) Prior Publication Data

US 2013/0190784 A1 Jul. 25, 2013

Related U.S. Application Data

(63) Continuation-in-part of application No. 12/891,962, filed on Sep. 28, 2010, now Pat. No. 8,758,373, which is a continuation-in-part of application No. 12/834,456, filed on Jul. 12, 2010, now Pat. No.
(Continued)

(30) Foreign Application Priority Data

Feb. 18, 2009 (WO) .................. PCT/IL2009/000188

(51) Int. Cl.
*A61F 2/00* (2006.01)
*A61B 17/00* (2006.01)
(Continued)

(52) U.S. Cl.
CPC ......... *A61F 2/0063* (2013.01); *A61B 17/00234* (2013.01); *A61B 17/064* (2013.01); *A61B 17/0643* (2013.01); *A61B 17/0686* (2013.01); *A61B 2017/00292* (2013.01); *A61F 2002/0072* (2013.01)

(58) Field of Classification Search
CPC ....................... A61F 2/0063; A61F 2002/0072
USPC .................................................. 606/151, 213
See application file for complete search history.

(56) References Cited

U.S. PATENT DOCUMENTS 4,347,847 A 9/1982 Usher
4,400,833 A 8/1983 Kurland
(Continued)

FOREIGN PATENT DOCUMENTS

CA 2413904 A1 6/2003
EP 328421 A2 8/1989
(Continued)

OTHER PUBLICATIONS

US 5,318,559, 04/1994, Green et al. (withdrawn).
(Continued)

*Primary Examiner* — Todd J Scherbel

(57) ABSTRACT

A system for closing an aperture in a biological tissue includes an implant deployment device with a frame arm and a clip operably disposed on the frame arm. A mesh attachment apparatus has a clip press with a body portion including a recess and at least one chamfered press operably disposed in the recess. The chamfered press is configured to move between an extended position protruding at least partially from said recess and a retracted position. The mesh attachment apparatus is configured to move the clip from an open position to a closed position to facilitate loading an implant onto the implant deployment device.

15 Claims, 28 Drawing Sheets

Related U.S. Application Data 8,753,359, which is a continuation-in-part of application No. PCT/IL2009/000188, filed on Feb. 18, 2009.

(60) Provisional application No. 61/029,386, filed on Feb. 18, 2008.

(51) Int. Cl.
*A61B 17/064* (2006.01)
*A61B 17/068* (2006.01)

(56) References Cited

U.S. PATENT DOCUMENTS

| | | | |
|---|---|---|---|
| 4,452,245 A | 6/1984 | Usher | |
| 4,485,816 A | 12/1984 | Krumme | |
| 4,585,458 A | 4/1986 | Kurland | |
| 4,633,873 A | 1/1987 | Dumican et al. | |
| 4,838,884 A | 6/1989 | Dumican et al. | |
| 4,854,316 A | 8/1989 | Davis | |
| 4,930,674 A * | 6/1990 | Barak | 227/179.1 |
| 5,019,096 A | 5/1991 | Fox, Jr. et al. | |
| 5,116,357 A | 5/1992 | Eberbach | |
| 5,122,155 A | 6/1992 | Eberbach | |
| 5,125,553 A | 6/1992 | Oddsen et al. | |
| 5,141,515 A | 8/1992 | Eberbach | |
| 5,147,374 A | 9/1992 | Fernandez | |
| 5,176,692 A | 1/1993 | Wilk et al. | |
| 5,203,864 A | 4/1993 | Phillips | |
| 5,219,077 A | 6/1993 | Transue | |
| 5,249,682 A | 10/1993 | Transue | |
| 5,254,133 A | 10/1993 | Seid | |
| 5,258,000 A | 11/1993 | Gianturco | |
| 5,263,969 A | 11/1993 | Phillips | |
| 5,289,963 A | 3/1994 | McGarry et al. | |
| 5,290,217 A | 3/1994 | Campos | |
| 5,292,328 A | 3/1994 | Hain et al. | |
| 5,304,187 A | 4/1994 | Green et al. | |
| 5,318,599 A | 6/1994 | Lorenz et al. | |
| 5,333,624 A | 8/1994 | Tovey | |
| 5,354,292 A | 10/1994 | Braeuer et al. | |
| 5,356,064 A | 10/1994 | Green et al. | |
| 5,356,432 A | 10/1994 | Rutkow et al. | |
| 5,364,002 A | 11/1994 | Green et al. | |
| 5,364,004 A | 11/1994 | Davidson | |
| 5,366,460 A | 11/1994 | Eberbach | |
| 5,368,602 A | 11/1994 | de la Torre | |
| 5,370,650 A | 12/1994 | Tovey et al. | |
| 5,376,097 A | 12/1994 | Phillips | |
| 5,383,477 A | 1/1995 | DeMatteis | |
| 5,392,978 A | 2/1995 | Velez et al. | |
| 5,395,383 A | 3/1995 | Adams et al. | |
| 5,397,331 A | 3/1995 | Himpens et al. | |
| 5,397,332 A | 3/1995 | Kammerer et al. | |
| 5,405,360 A | 4/1995 | Tovey | |
| 5,425,357 A | 6/1995 | Moll et al. | |
| 5,425,740 A | 6/1995 | Hutchinson, Jr. | |
| 5,433,996 A | 7/1995 | Kranzler et al. | |
| 5,464,403 A | 11/1995 | Kieturakis et al. | |
| 5,497,933 A | 3/1996 | DeFonzo et al. | |
| 5,531,759 A | 7/1996 | Kensey et al. | |
| 5,560,224 A | 10/1996 | Tessler | |
| 5,560,532 A | 10/1996 | DeFonzo et al. | |
| 5,564,615 A | 10/1996 | Bishop et al. | |
| 5,569,273 A | 10/1996 | Titone et al. | |
| 5,577,654 A | 11/1996 | Bishop | |
| 5,588,580 A | 12/1996 | Paul et al. | |
| 5,588,581 A | 12/1996 | Conlon et al. | |
| 5,601,224 A | 2/1997 | Bishop et al. | |
| 5,614,284 A | 3/1997 | Kranzler et al. | |
| 5,618,290 A | 4/1997 | Toy et al. | |
| 5,626,587 A | 5/1997 | Bishop et al. | |
| 5,634,584 A | 6/1997 | Okorocha et al. | |
| 5,634,931 A | 6/1997 | Kugel | |
| 5,662,662 A | 9/1997 | Bishop et al. | |
| 5,695,525 A | 12/1997 | Mulhauser et al. | |
| 5,716,409 A | 2/1998 | Debbas | |
| 5,725,577 A | 3/1998 | Saxon | |
| 5,728,119 A | 3/1998 | Smith et al. | |
| 5,749,895 A | 5/1998 | Sawyer et al. | |
| 5,766,246 A | 6/1998 | Mulhauser et al. | |
| 5,769,864 A | 6/1998 | Kugel | |
| 5,779,728 A | 7/1998 | Lunsford et al. | |
| 5,803,902 A | 9/1998 | Sienkiewicz et al. | |
| 5,810,851 A | 9/1998 | Yoon | |
| 5,814,058 A | 9/1998 | Carlson et al. | |
| 5,817,109 A | 10/1998 | McGarry et al. | |
| 5,824,082 A | 10/1998 | Brown | |
| 5,836,961 A | 11/1998 | Kieturakis et al. | |
| 5,854,383 A | 12/1998 | Erneta et al. | |
| 5,863,531 A | 1/1999 | Naughton et al. | |
| 5,865,728 A | 2/1999 | Moll et al. | |
| 5,911,726 A | 6/1999 | Belknap | |
| 5,916,225 A | 6/1999 | Kugel | |
| 5,925,058 A | 7/1999 | Smith et al. | |
| 5,937,951 A * | 8/1999 | Izuchukwu et al. | 227/176.1 |
| 5,951,997 A | 9/1999 | Bezwada et al. | |
| 5,954,767 A | 9/1999 | Pajotin et al. | |
| 5,957,939 A | 9/1999 | Heaven et al. | |
| 5,972,007 A | 10/1999 | Sheffield et al. | |
| 5,972,008 A | 10/1999 | Kalinski et al. | |
| 5,990,378 A | 11/1999 | Ellis | |
| 6,004,333 A | 12/1999 | Sheffield et al. | |
| 6,042,592 A | 3/2000 | Schmitt | |
| 6,066,776 A | 5/2000 | Goodwin et al. | |
| 6,066,777 A | 5/2000 | Benchetrit | |
| 6,068,635 A | 5/2000 | Gianotti | |
| 6,090,116 A | 7/2000 | D'Aversa et al. | |
| 6,113,609 A | 9/2000 | Adams | |
| 6,113,611 A | 9/2000 | Allen et al. | |
| 6,113,624 A | 9/2000 | Bezwada et al. | |
| 6,166,286 A | 12/2000 | Trabucco | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,197,036 B1 | 3/2001 | Tripp et al. | |
| 6,214,020 B1 | 4/2001 | Mulhauser et al. | |
| 6,224,616 B1 | 5/2001 | Kugel | |
| 6,241,768 B1 | 6/2001 | Agarwal et al. | |
| 6,258,113 B1 | 7/2001 | Adams et al. | |
| 6,258,124 B1 | 7/2001 | Darois et al. | |
| 6,267,772 B1 | 7/2001 | Mulhauser et al. | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,293,906 B1 | 9/2001 | Vanden Hoek et al. | |
| 6,312,442 B1 | 11/2001 | Kieturakis et al. | |
| 6,319,264 B1 | 11/2001 | Tormala et al. | |
| 6,368,541 B1 | 4/2002 | Pajotin et al. | |
| 6,375,662 B1 | 4/2002 | Schmitt | |
| 6,383,201 B1 | 5/2002 | Dong | |
| 6,391,060 B1 | 5/2002 | Ory et al. | |
| 6,408,656 B1 | 6/2002 | Ory et al. | |
| 6,416,486 B1 | 7/2002 | Wampler | |
| 6,425,900 B1 | 7/2002 | Knodel et al. | |
| 6,425,924 B1 | 7/2002 | Rousseau | |
| 6,436,030 B2 | 8/2002 | Rehil | |
| 6,447,524 B1 | 9/2002 | Knodel et al. | |
| 6,478,803 B1 | 11/2002 | Kapec et al. | |
| 6,485,503 B2 | 11/2002 | Jacobs et al. | |
| 6,497,650 B1 | 12/2002 | Nicolo | |
| 6,517,584 B1 | 2/2003 | Lecalve | |
| 6,527,785 B2 | 3/2003 | Sancoff et al. | |
| 6,551,241 B1 | 4/2003 | Schultz | |
| 6,551,333 B2 | 4/2003 | Kuhns et al. | |
| 6,558,400 B2 | 5/2003 | Deem et al. | |
| 6,565,590 B2 | 5/2003 | Kieturakis et al. | |
| 6,575,988 B2 | 6/2003 | Rousseau | |
| 6,607,541 B1 | 8/2003 | Gardiner et al. | |
| 6,610,006 B1 | 8/2003 | Amid et al. | |
| 6,613,059 B2 | 9/2003 | Schaller et al. | |
| 6,613,072 B2 | 9/2003 | Lau et al. | |
| 6,616,685 B2 | 9/2003 | Rousseau | |
| 6,638,208 B1 | 10/2003 | Natarajan et al. | |
| 6,638,284 B1 | 10/2003 | Rousseau et al. | |

(56) References Cited

U.S. PATENT DOCUMENTS

| | | |
|---|---|---|
| 6,638,292 B2 | 10/2003 | Adams |
| 6,638,297 B1 | 10/2003 | Huitema |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,676,643 B2 | 1/2004 | Brushey |
| 6,689,047 B2 | 2/2004 | Gellman |
| 6,694,192 B2 | 2/2004 | Policker et al. |
| 6,695,856 B2 | 2/2004 | Kieturakis et al. |
| 6,709,442 B2 | 3/2004 | Miller et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,746,458 B1 | 6/2004 | Cloud |
| 6,755,867 B2 | 6/2004 | Rousseau |
| 6,773,438 B1 | 8/2004 | Knodel et al. |
| 6,783,554 B2 | 8/2004 | Amara et al. |
| 6,790,213 B2 | 9/2004 | Cherok et al. |
| 6,800,081 B2 | 10/2004 | Parodi |
| 6,800,082 B2 | 10/2004 | Rousseau |
| 6,805,669 B2 | 10/2004 | Swanbom |
| 6,833,408 B2 | 12/2004 | Sehl et al. |
| 6,837,893 B2 | 1/2005 | Miller |
| 6,893,452 B2 | 5/2005 | Jacobs |
| 6,913,607 B2 | 7/2005 | Ainsworth et al. |
| 6,913,622 B2 | 7/2005 | Gjunter |
| 6,936,052 B2 | 8/2005 | Gellman et al. |
| 6,945,980 B2 | 9/2005 | Nguyen et al. |
| 6,953,428 B2 | 10/2005 | Gellman et al. |
| 6,960,217 B2 | 11/2005 | Bolduc |
| 6,960,233 B1 | 11/2005 | Berg et al. |
| 6,966,916 B2 | 11/2005 | Kumar |
| 6,974,586 B2 | 12/2005 | Greenhalgh et al. |
| 6,991,597 B2 | 1/2006 | Gellman et al. |
| 7,001,405 B2 | 2/2006 | Kieturakis et al. |
| 7,011,688 B2 | 3/2006 | Gryska et al. |
| 7,025,772 B2 | 4/2006 | Gellman et al. |
| 7,049,345 B2 | 5/2006 | Holmes-Farley |
| 7,077,850 B2 | 7/2006 | Kortenbach |
| 7,083,629 B2 | 8/2006 | Weller et al. |
| 7,083,630 B2 | 8/2006 | DeVries et al. |
| 7,094,261 B2 | 8/2006 | Zotti et al. |
| 7,101,366 B2 | 9/2006 | Trout, III et al. |
| 7,101,381 B2 | 9/2006 | Ford et al. |
| 7,119,062 B1 | 10/2006 | Alvis et al. |
| 7,148,315 B2 | 12/2006 | Erneta et al. |
| 7,198,046 B1 | 4/2007 | Argenta et al. |
| 7,214,236 B2 | 5/2007 | Kieturakis et al. |
| 7,216,651 B2 | 5/2007 | Argenta et al. |
| 7,220,282 B2 | 5/2007 | Kuslich |
| 7,229,452 B2 | 6/2007 | Kayan |
| 7,235,043 B2 | 6/2007 | Gellman et al. |
| 7,235,295 B2 | 6/2007 | Laurencin et al. |
| 7,255,675 B2 | 8/2007 | Gertner et al. |
| 7,320,325 B2 | 1/2008 | Duchon et al. |
| 7,331,199 B2 | 2/2008 | Ory et al. |
| 7,381,225 B2 | 6/2008 | Croce et al. |
| 7,404,819 B1 | 7/2008 | Darios et al. |
| 7,406,969 B2 | 8/2008 | Duchon et al. |
| 7,407,480 B2 | 8/2008 | Staskin et al. |
| 7,485,129 B2 | 2/2009 | Eisenkolb |
| 7,491,232 B2 | 2/2009 | Bolduc et al. |
| 7,500,945 B2 | 3/2009 | Cox et al. |
| 7,500,993 B2 | 3/2009 | de la Torre et al. |
| 7,524,333 B2 | 4/2009 | Lambrecht et al. |
| 7,544,213 B2 | 6/2009 | Adams |
| 7,553,329 B2 | 6/2009 | Lambrecht et al. |
| 7,553,330 B2 | 6/2009 | Lambrecht et al. |
| RE40,833 E | 7/2009 | Wintermantel et al. |
| 7,566,337 B2 | 7/2009 | Sogaard-Andersen et al. |
| 7,594,921 B2 | 9/2009 | Browning |
| 7,601,118 B2 | 10/2009 | Smith et al. |
| 7,601,172 B2 | 10/2009 | Segal et al. |
| 7,819,797 B2 | 10/2010 | Vanden Hoek et al. |
| 8,097,008 B2 | 1/2012 | Henderson |
| 8,317,808 B2 | 11/2012 | Levin et al. |
| 8,734,473 B2 | 5/2014 | Levin et al. |
| 8,753,359 B2 | 6/2014 | Levin et al. |
| 8,753,361 B2 * | 6/2014 | Abuzaina et al. .............. 606/151 |
| 8,758,373 B2 * | 6/2014 | Levin et al. ................... 606/151 |
| 8,808,314 B2 | 8/2014 | Levin et al. |
| 9,005,241 B2 | 4/2015 | Levin et al. |
| 2001/0016754 A1 | 8/2001 | Adams et al. |
| 2001/0018592 A1 | 8/2001 | Schaller et al. |
| 2001/0018593 A1 | 8/2001 | Nguyen et al. |
| 2001/0027347 A1 | 10/2001 | Rousseau |
| 2001/0044637 A1 | 11/2001 | Jacobs et al. |
| 2001/0049538 A1 | 12/2001 | Trabucco |
| 2001/0049539 A1 | 12/2001 | Rehil |
| 2001/0053919 A1 | 12/2001 | Kieturakis et al. |
| 2001/0056275 A1 | 12/2001 | Brushey |
| 2002/0010457 A1 | 1/2002 | Duchon et al. |
| 2002/0010480 A1 | 1/2002 | Sancoff et al. |
| 2002/0010490 A1 | 1/2002 | Schaller et al. |
| 2002/0010494 A1 | 1/2002 | Policker et al. |
| 2002/0029048 A1 | 3/2002 | Miller |
| 2002/0042658 A1 | 4/2002 | Tyagi |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0052654 A1 | 5/2002 | Darois et al. |
| 2002/0058967 A1 | 5/2002 | Jervis |
| 2002/0065524 A1 | 5/2002 | Miller et al. |
| 2002/0066360 A1 | 6/2002 | Greenhalgh et al. |
| 2002/0077652 A1 | 6/2002 | Kieturakis et al. |
| 2002/0082621 A1 | 6/2002 | Schurr et al. |
| 2002/0087170 A1 | 7/2002 | Kuhns et al. |
| 2002/0091405 A1 | 7/2002 | Kieturakis et al. |
| 2002/0103434 A1 | 8/2002 | Swanbom |
| 2002/0103494 A1 | 8/2002 | Pacey |
| 2002/0107539 A1 | 8/2002 | Kieturakis et al. |
| 2002/0116070 A1 | 8/2002 | Amara et al. |
| 2002/0117534 A1 | 8/2002 | Green et al. |
| 2002/0147457 A1 | 10/2002 | Rousseau |
| 2002/0165561 A1 | 11/2002 | Ainsworth et al. |
| 2002/0169452 A1 | 11/2002 | Tormala et al. |
| 2002/0173803 A1 | 11/2002 | Ainsworth et al. |
| 2002/0173804 A1 | 11/2002 | Rousseau |
| 2002/0183765 A1 | 12/2002 | Adams |
| 2002/0183768 A1 | 12/2002 | Deem et al. |
| 2002/0188317 A1 | 12/2002 | Rousseau |
| 2003/0004581 A1 | 1/2003 | Rousseau |
| 2003/0039626 A1 | 2/2003 | Holmes-Farley |
| 2003/0065359 A1 | 4/2003 | Weller et al. |
| 2003/0073976 A1 | 4/2003 | Brushey |
| 2003/0078602 A1 | 4/2003 | Rousseau |
| 2003/0078603 A1 | 4/2003 | Schaller et al. |
| 2003/0105473 A1 | 6/2003 | Miller |
| 2003/0109892 A1 | 6/2003 | Deem et al. |
| 2003/0119985 A1 | 6/2003 | Sehl et al. |
| 2003/0120265 A1 | 6/2003 | Deem et al. |
| 2003/0120299 A1 | 6/2003 | Kieturakis et al. |
| 2003/0130745 A1 | 7/2003 | Cherok et al. |
| 2003/0166628 A1 | 9/2003 | Doyle et al. |
| 2003/0171761 A1 | 9/2003 | Sancoff et al. |
| 2003/0171812 A1 | 9/2003 | Grunberg et al. |
| 2003/0171823 A1 | 9/2003 | Zotti et al. |
| 2003/0187516 A1 | 10/2003 | Amid et al. |
| 2003/0195531 A1 | 10/2003 | Gardiner et al. |
| 2003/0208211 A1 | 11/2003 | Kortenbach |
| 2003/0212460 A1 | 11/2003 | Darois et al. |
| 2003/0212461 A1 | 11/2003 | Vadurro et al. |
| 2003/0212462 A1 | 11/2003 | Gryska et al. |
| 2003/0220660 A1 | 11/2003 | Kortenbach et al. |
| 2003/0225355 A1 | 12/2003 | Butler |
| 2003/0225420 A1 | 12/2003 | Wardle |
| 2004/0002679 A1 | 1/2004 | Trout et al. |
| 2004/0010317 A1 | 1/2004 | Lambrecht et al. |
| 2004/0019360 A1 | 1/2004 | Farnsworth et al. |
| 2004/0024386 A1 | 2/2004 | Deem et al. |
| 2004/0024465 A1 | 2/2004 | Lambrecht et al. |
| 2004/0030217 A1 | 2/2004 | Yeung et al. |
| 2004/0039453 A1 | 2/2004 | Anderson et al. |

(56) References Cited

U.S. PATENT DOCUMENTS

| | | |
|---|---|---|
| 2004/0044364 A1 | 3/2004 | DeVries et al. |
| 2004/0044412 A1 | 3/2004 | Lambrecht et al. |
| 2004/0049227 A1 | 3/2004 | Jervis |
| 2004/0049282 A1 | 3/2004 | Gjunter |
| 2004/0054376 A1 | 3/2004 | Ory et al. |
| 2004/0059356 A1 | 3/2004 | Gingras |
| 2004/0064131 A1 | 4/2004 | Brushey |
| 2004/0073237 A1 | 4/2004 | Leinsing |
| 2004/0073257 A1 | 4/2004 | Spitz |
| 2004/0082755 A1 | 4/2004 | Erneta et al. |
| 2004/0087970 A1 | 5/2004 | Chu et al. |
| 2004/0087979 A1 | 5/2004 | Field et al. |
| 2004/0087980 A1 | 5/2004 | Ford et al. |
| 2004/0092937 A1 | 5/2004 | Criscuolo et al. |
| 2004/0092969 A1 | 5/2004 | Kumar |
| 2004/0092970 A1 | 5/2004 | Xavier |
| 2004/0097924 A1 | 5/2004 | Lambrecht et al. |
| 2004/0097986 A1 | 5/2004 | Adams |
| 2004/0122452 A1 | 6/2004 | Deem et al. |
| 2004/0122453 A1 | 6/2004 | Deem et al. |
| 2004/0133214 A1 | 7/2004 | Kayan |
| 2004/0144395 A1 | 7/2004 | Evans et al. |
| 2004/0152977 A1 | 8/2004 | Duchon et al. |
| 2004/0152978 A1 | 8/2004 | Duchon et al. |
| 2004/0172048 A1 | 9/2004 | Browning |
| 2004/0181288 A1 | 9/2004 | Darois et al. |
| 2004/0193043 A1 | 9/2004 | Duchon et al. |
| 2004/0215219 A1 | 10/2004 | Eldridge et al. |
| 2004/0225247 A1 | 11/2004 | Pugsley et al. |
| 2004/0225373 A1 | 11/2004 | Pugsley et al. |
| 2004/0230208 A1 | 11/2004 | Shayani |
| 2004/0234576 A1 | 11/2004 | Martin et al. |
| 2004/0249412 A1 | 12/2004 | Snow et al. |
| 2004/0254592 A1 | 12/2004 | DiCarlo et al. |
| 2005/0004427 A1 | 1/2005 | Cervigni |
| 2005/0010239 A1 | 1/2005 | Chefitz |
| 2005/0010306 A1 | 1/2005 | Priewe et al. |
| 2005/0015102 A1 | 1/2005 | Chefitz |
| 2005/0019436 A1 | 1/2005 | Burch et al. |
| 2005/0021058 A1 | 1/2005 | Negro |
| 2005/0021122 A1 | 1/2005 | Eisenkolb |
| 2005/0027369 A1 | 2/2005 | Eldridge et al. |
| 2005/0033318 A1 | 2/2005 | Miller et al. |
| 2005/0038452 A1 | 2/2005 | Chu |
| 2005/0054771 A1 | 3/2005 | Sehl et al. |
| 2005/0055097 A1 | 3/2005 | Grunberg et al. |
| 2005/0060038 A1 | 3/2005 | Lambrecht et al. |
| 2005/0065072 A1 | 3/2005 | Keeler et al. |
| 2005/0075667 A1 | 4/2005 | Schaller et al. |
| 2005/0080454 A1 | 4/2005 | Drews et al. |
| 2005/0113849 A1 | 5/2005 | Popadiuk et al. |
| 2005/0113858 A1 | 5/2005 | Deutsch |
| 2005/0118239 A1 | 6/2005 | Sabesan |
| 2005/0129733 A1 | 6/2005 | Milbocker et al. |
| 2005/0142315 A1 | 6/2005 | DeSimone et al. |
| 2005/0143817 A1 | 6/2005 | Hunter et al. |
| 2005/0149072 A1 | 7/2005 | DeVries et al. |
| 2005/0149080 A1 | 7/2005 | Hunter et al. |
| 2005/0149158 A1 | 7/2005 | Hunter et al. |
| 2005/0154361 A1 | 7/2005 | Sabesan |
| 2005/0159777 A1 | 7/2005 | Spitz |
| 2005/0165425 A1 | 7/2005 | Croce et al. |
| 2005/0165488 A1 | 7/2005 | Hunter et al. |
| 2005/0169959 A1 | 8/2005 | Hunter et al. |
| 2005/0175663 A1 | 8/2005 | Hunter et al. |
| 2005/0177225 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0183728 A1 | 8/2005 | Hunter et al. |
| 2005/0191331 A1 | 9/2005 | Hunter et al. |
| 2005/0192600 A1 | 9/2005 | Nicolo et al. |
| 2005/0202067 A1 | 9/2005 | Lendlein et al. |
| 2005/0222591 A1 | 10/2005 | Gingras et al. |
| 2005/0228408 A1 | 10/2005 | Fricke et al. |
| 2005/0234557 A1 | 10/2005 | Lambrecht et al. |
| 2005/0240269 A1 | 10/2005 | Lambrecht et al. |
| 2005/0244455 A1 | 11/2005 | Greenawalt |
| 2005/0245787 A1 | 11/2005 | Cox et al. |
| 2005/0249770 A1 | 11/2005 | Hunter |
| 2005/0256532 A1 | 11/2005 | Nayak et al. |
| 2005/0267325 A1 | 12/2005 | Bouchier et al. |
| 2005/0271794 A1 | 12/2005 | DeSimone et al. |
| 2005/0273146 A1 | 12/2005 | DeSimone et al. |
| 2005/0283119 A1 | 12/2005 | Uth et al. |
| 2005/0283189 A1 | 12/2005 | Rosenblatt |
| 2005/0283190 A1 | 12/2005 | Huitema et al. |
| 2005/0283246 A1 | 12/2005 | Cauthen et al. |
| 2005/0283962 A1 | 12/2005 | Boudjemline |
| 2005/0288691 A1 | 12/2005 | Leiboff |
| 2005/0288775 A1 | 12/2005 | Dong |
| 2006/0009802 A1 | 1/2006 | Modesitt |
| 2006/0015142 A1 | 1/2006 | Malazgirt |
| 2006/0015143 A1 | 1/2006 | Alvarado |
| 2006/0024238 A1 | 2/2006 | Barth et al. |
| 2006/0025649 A1 | 2/2006 | Smith et al. |
| 2006/0039896 A1 | 2/2006 | Kleinsek et al. |
| 2006/0047180 A1 | 3/2006 | Hegde et al. |
| 2006/0052816 A1 | 3/2006 | Bates et al. |
| 2006/0064175 A1 | 3/2006 | Pelissier et al. |
| 2006/0079558 A1 | 4/2006 | Aberg et al. |
| 2006/0079559 A1 | 4/2006 | Aberg et al. |
| 2006/0083710 A1 | 4/2006 | Joerger et al. |
| 2006/0105026 A1 | 5/2006 | Fortune et al. |
| 2006/0116696 A1 | 6/2006 | Odermatt et al. |
| 2006/0122637 A1 | 6/2006 | Barker |
| 2006/0127353 A1 | 6/2006 | Holmes-Farley |
| 2006/0129152 A1 | 6/2006 | Shipp |
| 2006/0129154 A1 | 6/2006 | Shipp |
| 2006/0142787 A1 | 6/2006 | Weller et al. |
| 2006/0147488 A1 | 7/2006 | Wohlert |
| 2006/0147492 A1 | 7/2006 | Hunter et al. |
| 2006/0149316 A1 | 7/2006 | DeVries et al. |
| 2006/0155165 A1 | 7/2006 | Vanden Hoek et al. |
| 2006/0155379 A1 | 7/2006 | Heneveld et al. |
| 2006/0177489 A1 | 8/2006 | Massouda et al. |
| 2006/0189918 A1 | 8/2006 | Barker |
| 2006/0200246 A1 | 9/2006 | Lambrecht et al. |
| 2006/0206118 A1 | 9/2006 | Kim et al. |
| 2006/0206178 A1 | 9/2006 | Kim |
| 2006/0210602 A1 | 9/2006 | Sehl et al. |
| 2006/0217812 A1 | 9/2006 | Lambrecht et al. |
| 2006/0228391 A1 | 10/2006 | Seyedin et al. |
| 2006/0233852 A1 | 10/2006 | Milbocker |
| 2006/0240063 A9 | 10/2006 | Hunter et al. |
| 2006/0251702 A1 | 11/2006 | Janis et al. |
| 2006/0253203 A1 | 11/2006 | Alvarado |
| 2006/0264698 A1 | 11/2006 | Kondonis et al. |
| 2006/0282103 A1 | 12/2006 | Fricke et al. |
| 2006/0282105 A1 | 12/2006 | Ford et al. |
| 2006/0287729 A1 | 12/2006 | Segal et al. |
| 2006/0287730 A1 | 12/2006 | Segal et al. |
| 2007/0016300 A1 | 1/2007 | Kuslich |
| 2007/0021756 A1 | 1/2007 | Kortenbach |
| 2007/0026043 A1 | 2/2007 | Guan et al. |
| 2007/0027358 A1 | 2/2007 | Gertner et al. |
| 2007/0032881 A1 | 2/2007 | Browning |
| 2007/0036876 A1 | 2/2007 | Burch et al. |
| 2007/0038220 A1 | 2/2007 | Shipp |
| 2007/0038310 A1 | 2/2007 | Guetty |
| 2007/0100355 A1 | 5/2007 | Bonde et al. |
| 2007/0110786 A1 | 5/2007 | Tenney et al. |
| 2007/0111937 A1 | 5/2007 | Pickar et al. |
| 2007/0118133 A1 | 5/2007 | Lambrecht et al. |
| 2007/0118158 A1 | 5/2007 | Deem et al. |
| 2007/0118159 A1 | 5/2007 | Deem et al. |
| 2007/0122425 A1 | 5/2007 | Keeler et al. |
| 2007/0134292 A1 | 6/2007 | Suokas et al. |
| 2007/0135929 A1 | 6/2007 | Williams et al. |
| 2007/0156245 A1 | 7/2007 | Cauthen et al. |
| 2007/0162030 A1 | 7/2007 | Aranyi et al. |
| 2007/0162135 A1 | 7/2007 | Segal et al. |
| 2007/0167963 A1 | 7/2007 | Deem et al. |
| 2007/0173864 A1 | 7/2007 | Chu |

(56) References Cited

U.S. PATENT DOCUMENTS

| | | | |
|---|---|---|---|
| 2007/0173888 A1 | 7/2007 | Gertner et al. |
| 2007/0179335 A1 | 8/2007 | Gertner et al. |
| 2007/0184277 A1 | 8/2007 | Schussler et al. |
| 2007/0185506 A1 | 8/2007 | Jackson |
| 2007/0185541 A1 | 8/2007 | DiUbaldi et al. |
| 2007/0198040 A1 | 8/2007 | Buevich et al. |
| 2007/0202148 A1 | 8/2007 | Ringeisen et al. |
| 2007/0202173 A1 | 8/2007 | Cueto-Garcia |
| 2007/0203507 A1 | 8/2007 | McLaughlin et al. |
| 2007/0207186 A1 | 9/2007 | Scanlon et al. |
| 2007/0208358 A1 | 9/2007 | Kayan |
| 2007/0219569 A1 | 9/2007 | Shayani |
| 2007/0225791 A1 | 9/2007 | Molitor et al. |
| 2007/0244502 A1 | 10/2007 | Deutsch |
| 2007/0250087 A1 | 10/2007 | Makower et al. |
| 2007/0250147 A1 | 10/2007 | Walther et al. |
| 2007/0260179 A1 | 11/2007 | Sholev et al. |
| 2007/0260268 A1 | 11/2007 | Bartee et al. |
| 2007/0265710 A1 | 11/2007 | Brown et al. |
| 2007/0270752 A1 | 11/2007 | LaBombard |
| 2007/0280990 A1 | 12/2007 | Stopek |
| 2007/0293717 A1 | 12/2007 | Kaleta et al. |
| 2007/0293878 A1 | 12/2007 | Butsch |
| 2007/0299300 A1 | 12/2007 | Smith et al. |
| 2007/0299542 A1 | 12/2007 | Mathisen et al. |
| 2008/0015501 A1 | 1/2008 | Gertner |
| 2008/0021545 A1 | 1/2008 | Reneker et al. |
| 2008/0033461 A1 | 2/2008 | Koeckerling et al. |
| 2008/0035243 A1 | 2/2008 | Breitenkamp et al. |
| 2008/0045952 A1 | 2/2008 | Kuslich |
| 2008/0065229 A1 | 3/2008 | Adams |
| 2008/0086216 A1 | 4/2008 | Wilson et al. |
| 2008/0091222 A1 | 4/2008 | Deusch et al. |
| 2008/0091276 A1 | 4/2008 | Deusch et al. |
| 2008/0103351 A1 | 5/2008 | Montpetit et al. |
| 2008/0113035 A1 | 5/2008 | Hunter |
| 2008/0125869 A1 | 5/2008 | Paz et al. |
| 2008/0131509 A1 | 6/2008 | Hossainy et al. |
| 2008/0132602 A1 | 6/2008 | Rizk et al. |
| 2008/0147198 A1 | 6/2008 | Cherok et al. |
| 2008/0147200 A1 | 6/2008 | Rousseau et al. |
| 2008/0167519 A1 | 7/2008 | St-Germain |
| 2008/0167667 A1 | 7/2008 | Criscuolo et al. |
| 2008/0167668 A1 | 7/2008 | Criscuolo et al. |
| 2008/0188874 A1 | 8/2008 | Henderson |
| 2008/0193494 A1 | 8/2008 | Sabesan |
| 2008/0195121 A1 | 8/2008 | Eldar et al. |
| 2008/0200979 A1 | 8/2008 | Dieck et al. |
| 2008/0215154 A1 | 9/2008 | Lambrecht et al. |
| 2008/0243149 A1 | 10/2008 | Kockerling et al. |
| 2008/0255593 A1 | 10/2008 | St-Germain |
| 2008/0260794 A1 | 10/2008 | Lauritzen et al. |
| 2008/0269896 A1 | 10/2008 | Cherok et al. |
| 2008/0281433 A1 | 11/2008 | Chang et al. |
| 2008/0287970 A1 | 11/2008 | Amato et al. |
| 2008/0306497 A1 | 12/2008 | Brown et al. |
| 2008/0312751 A1 | 12/2008 | Pugsley et al. |
| 2009/0004239 A1 | 1/2009 | Ladet et al. |
| 2009/0005867 A1 | 1/2009 | Lefranc et al. |
| 2009/0012350 A1 | 1/2009 | Tihon |
| 2009/0012546 A1 | 1/2009 | N'diaye et al. |
| 2009/0018559 A1 | 1/2009 | Buevich et al. |
| 2009/0030434 A1 | 1/2009 | Paz et al. |
| 2009/0030522 A1 | 1/2009 | Cauthen, III et al. |
| 2009/0030527 A1 | 1/2009 | Richter |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0036996 A1 | 2/2009 | Roeber |
| 2009/0062823 A1 | 3/2009 | Richter et al. |
| 2009/0069826 A1 | 3/2009 | Walther et al. |
| 2009/0105526 A1 | 4/2009 | Piroli Torelli et al. |
| 2009/0125041 A1 | 5/2009 | Dudai |
| 2009/0137864 A1 | 5/2009 | Cox et al. |
| 2009/0149875 A1 | 6/2009 | Abele et al. |
| 2009/0155332 A1 | 6/2009 | Sherry et al. |
| 2009/0157184 A1 | 6/2009 | Cauthen, III et al. |
| 2009/0157195 A1 | 6/2009 | Siedle |
| 2009/0162273 A1 | 6/2009 | Lawrynowicz et al. |
| 2009/0182190 A1 | 7/2009 | Dann |
| 2009/0182352 A1 | 7/2009 | Paz et al. |
| 2009/0187258 A1 | 7/2009 | Ip et al. |
| 2009/0192346 A1 | 7/2009 | Rosenblatt |
| 2009/0192528 A1 | 7/2009 | Higgins et al. |
| 2009/0198260 A1 | 8/2009 | Ford et al. |
| 2009/0204130 A1 | 8/2009 | Kantsevoy et al. |
| 2009/0204227 A1 | 8/2009 | Derwin et al. |
| 2009/0216075 A1 | 8/2009 | Bell et al. |
| 2009/0216104 A1 | 8/2009 | DeSimone et al. |
| 2009/0216264 A1 | 8/2009 | Friedman et al. |
| 2009/0216338 A1 | 8/2009 | Gingras et al. |
| 2009/0234379 A1 | 9/2009 | Rehnke |
| 2009/0234461 A1 | 9/2009 | Rehnke |
| 2009/0240342 A1 | 9/2009 | Lindh, Sr. et al. |
| 2009/0240343 A1 | 9/2009 | Adams |
| 2009/0248048 A1 | 10/2009 | Milbocker |
| 2009/0248092 A1 | 10/2009 | Bellas et al. |
| 2009/0254103 A1 | 10/2009 | Deutsch |
| 2009/0259094 A1 | 10/2009 | Bouchier et al. |
| 2009/0281563 A1 | 11/2009 | Newell et al. |
| 2010/0069930 A1 | 3/2010 | Roslin et al. |
| 2010/0312357 A1 | 12/2010 | Levin et al. |
| 2010/0318121 A1 | 12/2010 | Levin et al. |
| 2011/0004221 A1 | 1/2011 | Euteneuer et al. |
| 2011/0040310 A1* | 2/2011 | Levin et al. ............... 606/151 |
| 2011/0040311 A1 | 2/2011 | Levin et al. |
| 2011/0042210 A1 | 2/2011 | Kang et al. |
| 2011/0054500 A1 | 3/2011 | Levin et al. |
| 2011/0066166 A1* | 3/2011 | Levin et al. ............... 606/151 |
| 2011/0112560 A1 | 5/2011 | Sholev |
| 2011/0301701 A1 | 12/2011 | Padala et al. |
| 2012/0046740 A1 | 2/2012 | Paul et al. |
| 2012/0259347 A1* | 10/2012 | Abuzaina et al. ............. 606/142 |
| 2013/0018395 A1 | 1/2013 | Friedlander et al. |
| 2013/0190784 A1* | 7/2013 | Palmer et al. ................ 606/151 |
| 2013/0310637 A1* | 11/2013 | Iceman et al. ................ 600/37 |
| 2013/0310850 A1* | 11/2013 | Glick et al. ................. 606/142 |
| 2013/0310851 A1* | 11/2013 | Iceman et al. ............... 606/142 |
| 2013/0310852 A1* | 11/2013 | Bolduc et al. ............... 606/142 |
| 2013/0310857 A1* | 11/2013 | Iceman et al. ............... 606/151 |
| 2013/0310858 A1* | 11/2013 | Palmer et al. ................ 606/151 |

FOREIGN PATENT DOCUMENTS

| | | | |
|---|---|---|---|
| EP | 525791 A1 | 2/1993 |
| EP | 537769 A1 | 4/1993 |
| EP | 544485 A1 | 6/1993 |
| EP | 556018 A1 | 8/1993 |
| EP | 0557963 A1 | 9/1993 |
| EP | 557964 A1 | 9/1993 |
| EP | 573273 A2 | 12/1993 |
| EP | 579377 A2 | 1/1994 |
| EP | 581036 A1 | 2/1994 |
| EP | 614650 A2 | 9/1994 |
| EP | 0625334 A1 | 11/1994 |
| EP | 702934 A1 | 3/1996 |
| EP | 744162 A2 | 11/1996 |
| EP | 827724 A2 | 3/1998 |
| EP | 898944 A2 | 3/1999 |
| EP | 908482 A1 | 4/1999 |
| EP | 986993 A1 | 3/2000 |
| EP | 1060714 A2 | 12/2000 |
| EP | 1145693 A2 | 10/2001 |
| EP | 1181899 A2 | 2/2002 |
| EP | 1199037 A2 | 4/2002 |
| EP | 1199038 A2 | 4/2002 |
| EP | 1219265 A2 | 7/2002 |
| EP | 1306061 A2 | 5/2003 |
| EP | 1317904 A1 | 6/2003 |
| EP | 1366717 A1 | 12/2003 |
| EP | 1541183 A1 | 6/2005 |
| EP | 1607048 A1 | 12/2005 |
| EP | 1671604 A2 | 6/2006 |
| EP | 1674048 A1 | 6/2006 |

(56) References Cited

FOREIGN PATENT DOCUMENTS

| | | |
|---|---|---|
| EP | 1700579 A1 | 9/2006 |
| EP | 1704832 A2 | 9/2006 |
| EP | 1849440 A1 | 10/2007 |
| EP | 1867348 A2 | 12/2007 |
| EP | 1870056 A1 | 12/2007 |
| EP | 1990014 A2 | 11/2008 |
| EP | 2050474 A2 | 4/2009 |
| FR | 2789888 A1 | 2/1999 |
| FR | 2789888 A1 | 8/2000 |
| WO | 8204390 A1 | 12/1982 |
| WO | 92/06639 A2 | 4/1992 |
| WO | 9211824 A1 | 7/1992 |
| WO | 9219162 A2 | 11/1992 |
| WO | 9221293 A1 | 12/1992 |
| WO | 9303685 A1 | 3/1993 |
| WO | 9307922 A1 | 4/1993 |
| WO | 9309722 A1 | 5/1993 |
| WO | 9317635 A1 | 9/1993 |
| WO | 94/17747 A1 | 8/1994 |
| WO | 9419029 A1 | 9/1994 |
| WO | 9427535 A1 | 12/1994 |
| WO | 95/07666 A1 | 3/1995 |
| WO | 9530374 A1 | 11/1995 |
| WO | 9531140 A1 | 11/1995 |
| WO | 96/03091 A1 | 2/1996 |
| WO | 9603165 A1 | 2/1996 |
| WO | 9606634 A1 | 3/1996 |
| WO | 96/09795 A1 | 4/1996 |
| WO | 9631157 A1 | 10/1996 |
| WO | 9640307 A1 | 12/1996 |
| WO | 9702789 A1 | 1/1997 |
| WO | 9722371 A1 | 6/1997 |
| WO | 9732526 A1 | 9/1997 |
| WO | 97/35533 A1 | 10/1997 |
| WO | 9803713 A1 | 1/1998 |
| WO | 9811814 A2 | 3/1998 |
| WO | 9814134 A2 | 4/1998 |
| WO | 9816153 A1 | 4/1998 |
| WO | 9837813 A1 | 9/1998 |
| WO | 9903422 A1 | 1/1999 |
| WO | 9905992 A1 | 2/1999 |
| WO | 9916381 A1 | 4/1999 |
| WO | 99/51163 A1 | 10/1999 |
| WO | 9960931 A1 | 12/1999 |
| WO | 9962406 A2 | 12/1999 |
| WO | 9963051 A2 | 12/1999 |
| WO | 0007520 A1 | 2/2000 |
| WO | 0016822 A1 | 3/2000 |
| WO | 0056376 A1 | 9/2000 |
| WO | 0057796 A1 | 10/2000 |
| WO | 0057812 A1 | 10/2000 |
| WO | 0061033 A1 | 10/2000 |
| WO | 00/67663 A1 | 11/2000 |
| WO | 0071548 A1 | 11/2000 |
| WO | 0071549 A1 | 11/2000 |
| WO | 0108594 A1 | 2/2001 |
| WO | 0126588 A2 | 4/2001 |
| WO | 0154589 A1 | 8/2001 |
| WO | 0168653 A1 | 9/2001 |
| WO | 0170322 A1 | 9/2001 |
| WO | 0180788 A2 | 11/2001 |
| WO | 0180920 A2 | 11/2001 |
| WO | 0185058 A2 | 11/2001 |
| WO | 0185060 A1 | 11/2001 |
| WO | 0189390 A1 | 11/2001 |
| WO | 0189392 A2 | 11/2001 |
| WO | 02/07648 A1 | 1/2002 |
| WO | 0217771 A2 | 3/2002 |
| WO | 0217796 A1 | 3/2002 |
| WO | 0217797 A1 | 3/2002 |
| WO | 0219916 A1 | 3/2002 |
| WO | 0219923 A1 | 3/2002 |
| WO | 0222047 A1 | 3/2002 |
| WO | 0224080 A2 | 3/2002 |
| WO | 0226747 | 4/2002 |
| WO | 0230336 A2 | 4/2002 |
| WO | 0232346 A1 | 4/2002 |
| WO | 0234140 A2 | 5/2002 |
| WO | 0235990 A2 | 5/2002 |
| WO | 02058543 A2 | 8/2002 |
| WO | 02074199 | 9/2002 |
| WO | 02/078568 A1 | 10/2002 |
| WO | 02080779 A1 | 10/2002 |
| WO | 02080780 A1 | 10/2002 |
| WO | 02087425 A2 | 11/2002 |
| WO | 02091928 A1 | 11/2002 |
| WO | 02091953 A1 | 11/2002 |
| WO | 02096327 A2 | 12/2002 |
| WO | 03002029 A1 | 1/2003 |
| WO | 03002130 A1 | 1/2003 |
| WO | 03032867 A1 | 4/2003 |
| WO | 03059180 A2 | 7/2003 |
| WO | 03059201 A1 | 7/2003 |
| WO | 03059217 A1 | 7/2003 |
| WO | 03077730 A2 | 9/2003 |
| WO | 03082125 A1 | 10/2003 |
| WO | 03084410 A1 | 10/2003 |
| WO | 03088846 A1 | 10/2003 |
| WO | 03090633 A2 | 11/2003 |
| WO | 03092509 | 11/2003 |
| WO | 03094781 A1 | 11/2003 |
| WO | 03094783 A1 | 11/2003 |
| WO | 03094786 A1 | 11/2003 |
| WO | 03094787 A1 | 11/2003 |
| WO | 03096909 A1 | 11/2003 |
| WO | 03096929 A1 | 11/2003 |
| WO | 03097011 A1 | 11/2003 |
| WO | 03099160 A1 | 12/2003 |
| WO | 03103473 A2 | 12/2003 |
| WO | 2004004600 A1 | 1/2004 |
| WO | 2004006808 A2 | 1/2004 |
| WO | 2004012579 A2 | 2/2004 |
| WO | 2004012627 A1 | 2/2004 |
| WO | 2004019787 A2 | 3/2004 |
| WO | 2004019788 A2 | 3/2004 |
| WO | 2004024030 | 3/2004 |
| WO | 2004028547 A1 | 4/2004 |
| WO | 2004034924 A2 | 4/2004 |
| WO | 2004037123 A1 | 5/2004 |
| WO | 2004058286 A1 | 7/2004 |
| WO | 2004060425 A2 | 7/2004 |
| WO | 2004062529 A2 | 7/2004 |
| WO | 2004062530 A2 | 7/2004 |
| WO | 2004069866 A1 | 8/2004 |
| WO | 2004080348 A1 | 9/2004 |
| WO | WO 2004/080348 A1 | 9/2004 |
| WO | 2004087227 A1 | 10/2004 |
| WO | 2004093737 A1 | 11/2004 |
| WO | 2004098461 A2 | 11/2004 |
| WO | 2004098665 A1 | 11/2004 |
| WO | 2004100841 A1 | 11/2004 |
| WO | 2004101002 A2 | 11/2004 |
| WO | 2004103166 A2 | 12/2004 |
| WO | 2004103414 A2 | 12/2004 |
| WO | 2005003351 A1 | 1/2005 |
| WO | 2005004727 A1 | 1/2005 |
| WO | 2005007209 A1 | 1/2005 |
| WO | 2005/016389 A2 | 2/2005 |
| WO | 2005014634 A1 | 2/2005 |
| WO | 2005018494 A1 | 3/2005 |
| WO | 2005019241 A2 | 3/2005 |
| WO | 2005019315 A1 | 3/2005 |
| WO | 2005035548 A1 | 4/2005 |
| WO | 2005041784 A2 | 5/2005 |
| WO | 2005044143 A1 | 5/2005 |
| WO | 2005051172 A2 | 6/2005 |
| WO | 2005055958 A1 | 6/2005 |
| WO | 2005065324 A2 | 7/2005 |
| WO | 2005065552 A2 | 7/2005 |
| WO | 2005/082273 A1 | 9/2005 |
| WO | 2005079335 A2 | 9/2005 |
| WO | 2005082274 A1 | 9/2005 |
| WO | 2005094721 A1 | 10/2005 |
| WO | 2005099628 A2 | 10/2005 |

(56) References Cited

FOREIGN PATENT DOCUMENTS

| | | |
|---|---|---|
| WO | 2005102209 A1 | 11/2005 |
| WO | 2005105172 A1 | 11/2005 |
| WO | 2005110243 A2 | 11/2005 |
| WO | 2005110273 A1 | 11/2005 |
| WO | 2006002439 A1 | 1/2006 |
| WO | 2006008429 A1 | 1/2006 |
| WO | 2006012353 A2 | 2/2006 |
| WO | 2006013337 A2 | 2/2006 |
| WO | 2006014650 A2 | 2/2006 |
| WO | 2006015031 A2 | 2/2006 |
| WO | 2006026509 A2 | 3/2006 |
| WO | 2006034117 A1 | 3/2006 |
| WO | 2006036936 A2 | 4/2006 |
| WO | 2006037047 A2 | 4/2006 |
| WO | 2006040760 A2 | 4/2006 |
| WO | 2006044785 A1 | 4/2006 |
| WO | 2006047645 A2 | 5/2006 |
| WO | 2006048885 A1 | 5/2006 |
| WO | 2006082587 A2 | 8/2006 |
| WO | 2006086339 A2 | 8/2006 |
| WO | 2006092159 A1 | 9/2006 |
| WO | 2006092236 A1 | 9/2006 |
| WO | 2006102457 A2 | 9/2006 |
| WO | 2006116000 A2 | 11/2006 |
| WO | 2006119034 A2 | 11/2006 |
| WO | 2007004228 A1 | 1/2007 |
| WO | 2007011689 A2 | 1/2007 |
| WO | 2007017872 A2 | 2/2007 |
| WO | 2007021620 A2 | 2/2007 |
| WO | 2007021759 A2 | 2/2007 |
| WO | 2007021834 A1 | 2/2007 |
| WO | 2007025293 A2 | 3/2007 |
| WO | 2007025296 A2 | 3/2007 |
| WO | 2007025302 A2 | 3/2007 |
| WO | 2007030676 A2 | 3/2007 |
| WO | 2007034145 A2 | 3/2007 |
| WO | 2007050382 A1 | 5/2007 |
| WO | 2007051221 A1 | 5/2007 |
| WO | 2007055755 A1 | 5/2007 |
| WO | 2007070141 A1 | 6/2007 |
| WO | 2007072469 A2 | 6/2007 |
| WO | 2007081955 A1 | 7/2007 |
| WO | 2007087132 A1 | 8/2007 |
| WO | 2007087146 A2 | 8/2007 |
| WO | 2007115110 A2 | 10/2007 |
| WO | 2007129220 A2 | 11/2007 |
| WO | 2007133311 A2 | 11/2007 |
| WO | 2007136820 A2 | 11/2007 |
| WO | 2007137211 A2 | 11/2007 |
| WO | 2007143726 A2 | 12/2007 |
| WO | 2007144782 A2 | 12/2007 |
| WO | 2007146784 A2 | 12/2007 |
| WO | 2008006097 A2 | 1/2008 |
| WO | 2008016802 A1 | 2/2008 |
| WO | 2008026905 A2 | 3/2008 |
| WO | 2008030873 A2 | 3/2008 |
| WO | 2008030939 A2 | 3/2008 |
| WO | 2008045635 A2 | 4/2008 |
| WO | WO 2008/045635 A2 | 4/2008 |
| WO | 2008055028 A1 | 5/2008 |
| WO | 2008065653 A1 | 6/2008 |
| WO | 2008069919 A2 | 6/2008 |
| WO | 2008083484 A1 | 7/2008 |
| WO | 2008085825 A1 | 7/2008 |
| WO | 2008094217 A1 | 8/2008 |
| WO | 2008094842 A1 | 8/2008 |
| WO | 2008099382 A1 | 8/2008 |
| WO | 2008112437 A2 | 9/2008 |
| WO | 2008124056 A1 | 10/2008 |
| WO | 2008140989 A2 | 11/2008 |
| WO | 2008157497 A2 | 12/2008 |
| WO | 2008157777 A1 | 12/2008 |
| WO | 2009005625 A1 | 1/2009 |
| WO | 2009005634 A1 | 1/2009 |
| WO | 2009011824 A1 | 1/2009 |
| WO | 2009012001 A1 | 1/2009 |
| WO | 2009022348 A1 | 2/2009 |
| WO | 2009036094 A2 | 3/2009 |
| WO | 2009039371 A1 | 3/2009 |
| WO | 2009042442 A1 | 4/2009 |
| WO | 2009048314 A1 | 4/2009 |
| WO | 2009050717 A2 | 4/2009 |
| WO | 2009059005 A1 | 5/2009 |
| WO | 2009064845 A2 | 5/2009 |
| WO | 2009069119 A1 | 6/2009 |
| WO | 2009075786 A1 | 6/2009 |
| WO | 2009075932 A1 | 6/2009 |
| WO | 2009075933 A1 | 6/2009 |
| WO | 2009086446 A1 | 7/2009 |
| WO | 2009092294 A1 | 7/2009 |
| WO | 2009094015 A1 | 7/2009 |
| WO | 2009097380 A1 | 8/2009 |
| WO | 2009102792 A2 | 8/2009 |
| WO | 2009104182 A2 | 8/2009 |
| WO | 2009113972 A2 | 9/2009 |
| WO | 2009126781 A1 | 10/2009 |
| WO | 2010019655 A1 | 2/2010 |
| WO | 2011/021082 A1 | 2/2011 |
| WO | 2012/112565 A2 | 8/2012 |
| WO | WO 2012/112565 | 8/2012 |

OTHER PUBLICATIONS

International Search Report of International Application No. PCT/IB 11/00301, dated Jul. 15, 2011 (1 page).
Extended European Search Report corresponding to EP 13 16 4453.6, completed Jul. 29, 2013 and mailed Aug. 5, 2013; (7 pp).
Extended European Search Report corresponding to EP 13 16 4453.6, completed Jul. 29, 2013 and mailed Aug. 5, 2013.
European Search Report for EP 09713121 dated Jul. 29, 2013.
Japanese Official Action, and English translation, mailed May 19, 2015 in Application No. JP 2011-199478.
Japanese Office Action, and English language translation, mailed Jun. 2, 2015 from Application No. JP 2011-200614.
EP Examination Report dated Mar. 26, 2015 from Application No. EP 13181252.1.
European Search Report EP11250797.5 dated Jun. 25, 2012.
Extended European Search Report corresponding to EP 09 71 3121.3, completed Jul. 22, 2013 and mailed Jul. 29, 2013; (7 pp).
European Search Report for EP 11 25 0799, dated Mar. 21, 2013, 6 pages.
US 6,503,260, 01/2003, Schaller et al. (withdrawn)

\* cited by examiner

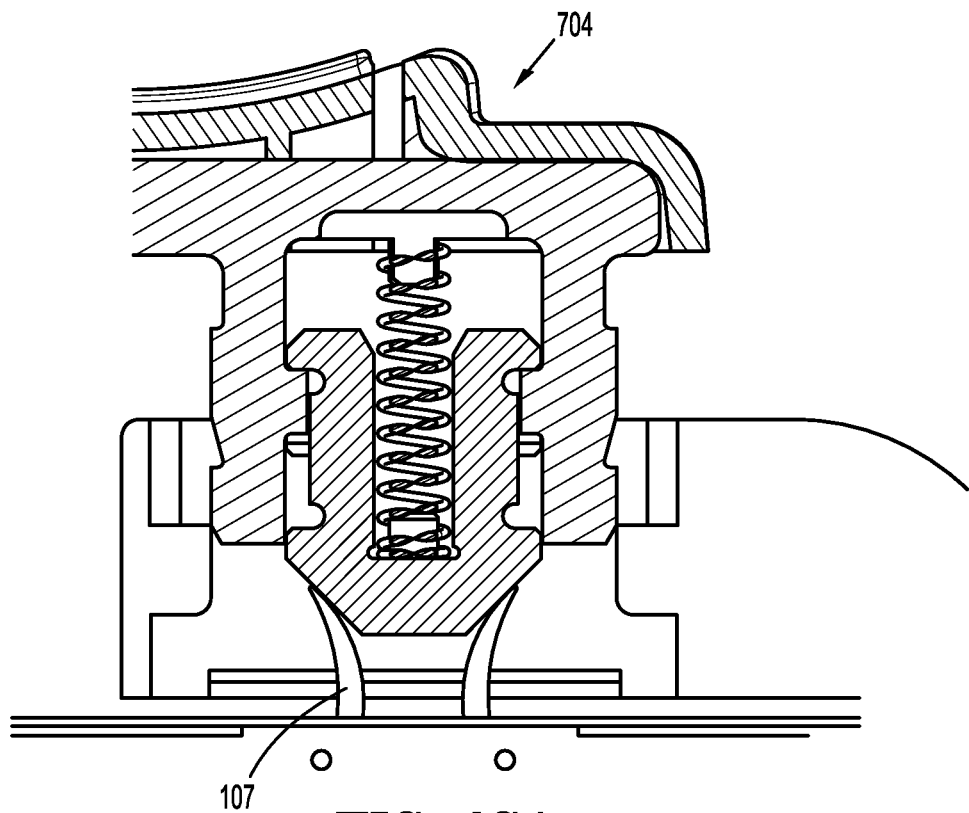
FIG. 4G1
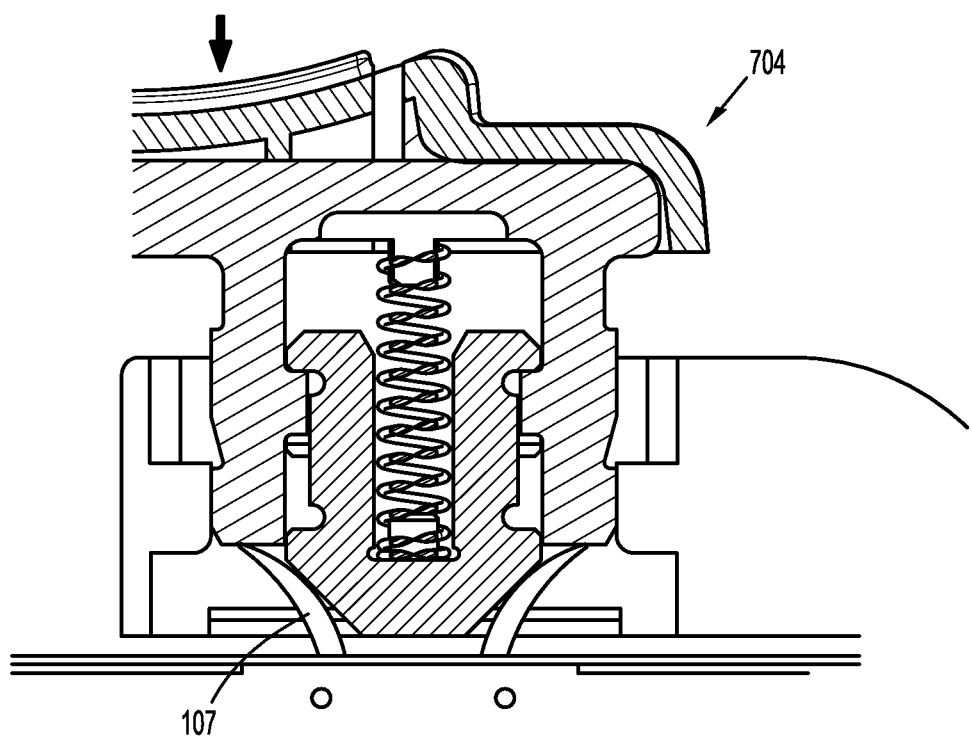
FIG. 4G2

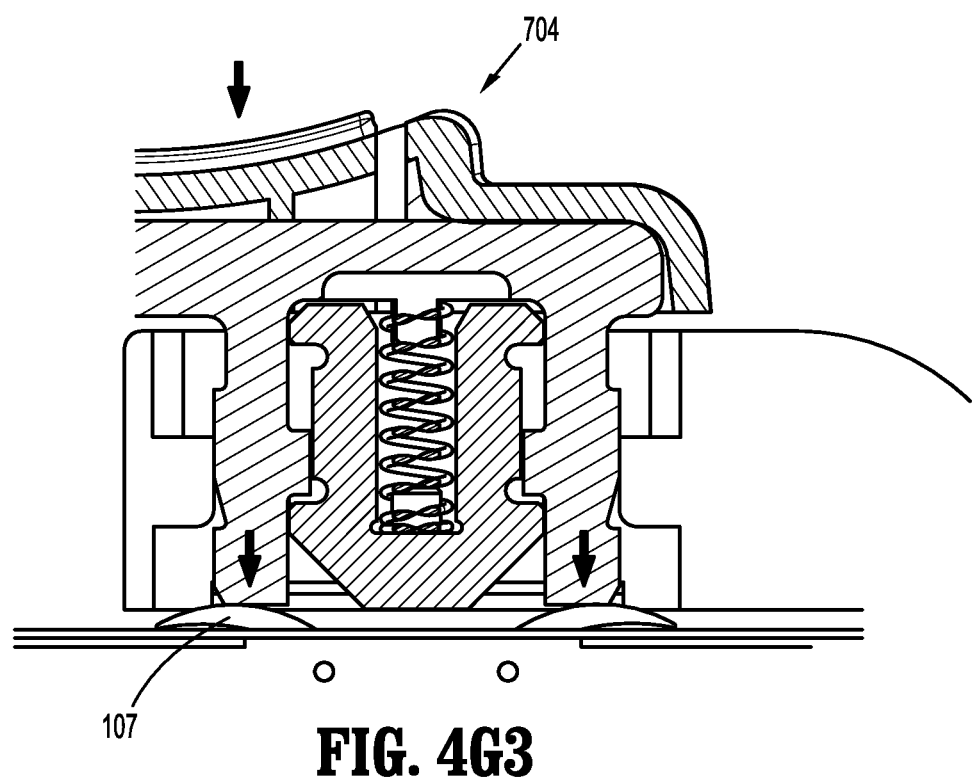
FIG. 4G3

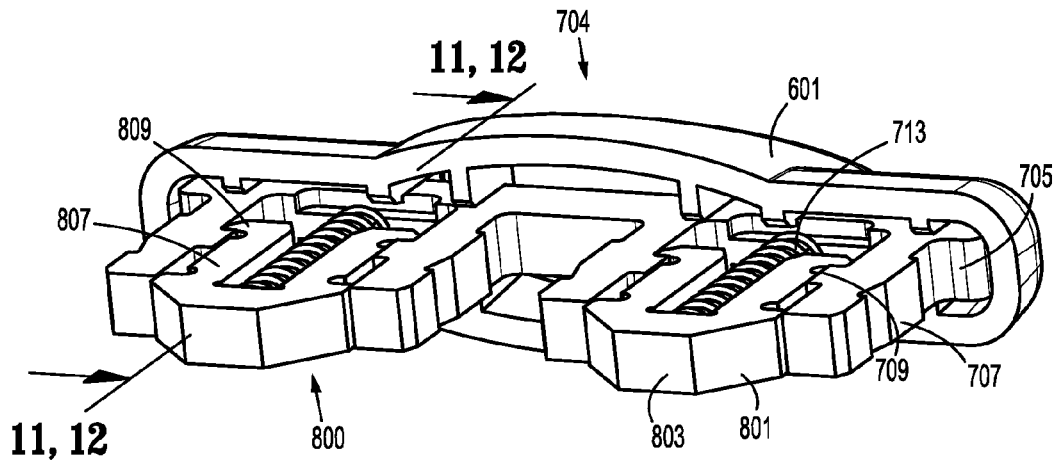
FIG. 10
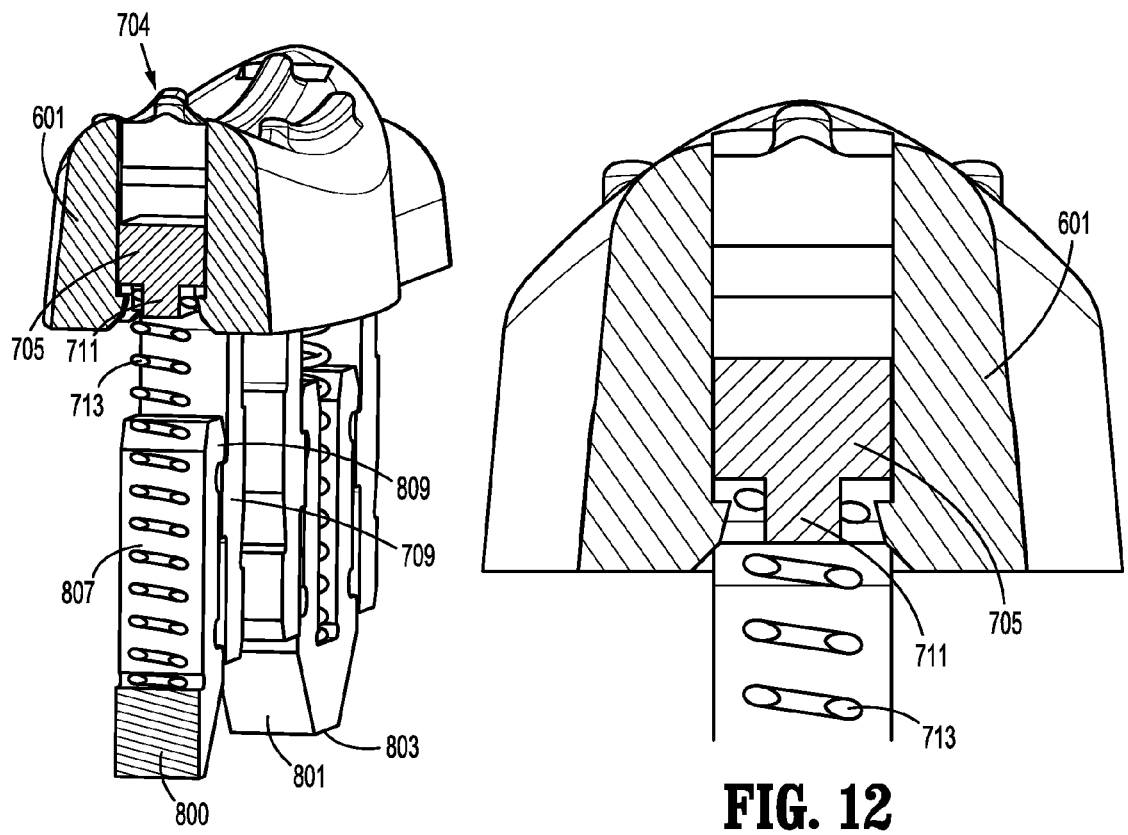
FIG. 11
FIG. 12

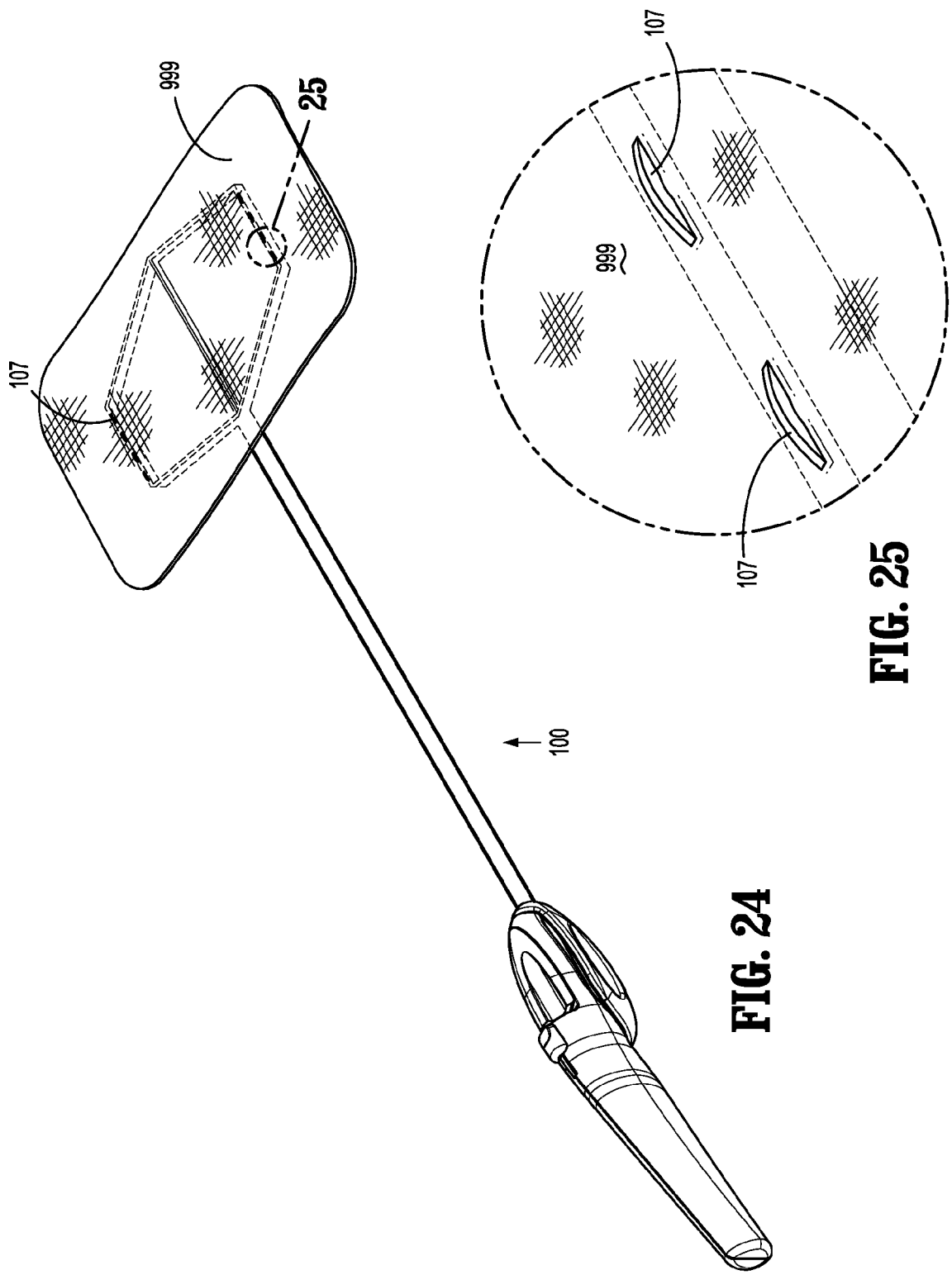

LOCK BAR SPRING AND CLIP FOR IMPLANT DEPLOYMENT DEVICE

CROSS-REFERENCE TO RELATED APPLICATIONS

The present application is a continuation-in-part of U.S. patent application Ser. No. 12/891,962, filed on Sep. 28, 2010, now U.S. Pat. No. 8,758,373, which is a continuation-in-part of U.S. patent application Ser. No. 12/834,456, filed Jul. 12, 2010, now U.S. Pat. No. 8,753,359, which is a continuation-in-part of PCT international patent application number PCT/IL2009/000188, filed Feb. 18, 2009, which claims the benefit of and priority to U.S. provisional patent application Ser. No. 61/029,386, filed Feb. 18, 2008. The present application also claims the benefit of and priority to U.S. provisional patent application Ser. No. 61/302,186, filed Feb. 8, 2010. The contents of each of these prior applications are incorporated by reference herein in their entirety.

FIELD OF THE INVENTION

This invention generally relates to a device and method for reversibly coupling an implant to an implant deployment device.

BACKGROUND

An object of the present invention is to provide an apparatus and a method for performing corrective surgery on internal wounds such as a hernia where invasion of the patient's body tissues is minimized and resultant trauma is reduced.

A hernia is a protrusion of a tissue, structure, or part of an organ through the muscular tissue or the membrane by which it is normally contained. In other words, a hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery, patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques, several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the implant and then to attach the implant to the tissue.

There are many patents and patent applications relating to attaching a prosthesis implant to a tissue via tacks. Each patent and patent application describes a different attachment mechanism via different anchoring means (see for example U.S. Pat. No. 6,447,524). Traditional anchors used in surgery include clips, staples, or sutures, and may also be referred to as tissue anchors. These devices are usually made of a biocompatible material (or are coated with a biocompatible material), so that they can be safely implanted into the body.

Most tissue anchors secure the tissue by impaling it with one or more posts or legs that are bent or crimped to lock the tissue into position. Thus, most traditional anchors are rigid or are inflexibly attached to the tissue. For example PCT No. WO 07/021834 describes an anchor having two curved legs that cross in a single turning direction to form a loop. Those two curved legs are adapted to penetrate tissue in a curved pathway. U.S. Pat. No. 4,485,816 describes surgical staple made of shape memory alloy. The staple is placed in contact of the tissue and then heated. The heating causes the staple to change its shape thus, penetrating the tissue.

U.S. Pat. No. 6,893,452 describes a tissue attachment device that facilitates wound healing by holding soft tissue together under improved distribution of tension and with minimal disruption of the wound interface and its nutrient supplies.

U.S. Pat. No. 6,517,584 describes a hernia implant which includes at least one anchoring device made of shape memory material. The anchoring devices are initially secured to the prosthesis by being interlaced through a web mesh constituting the prosthesis. The attachment is obtained by altering the attachment element's shape from rectilinear to a loop shape due to heat induced shape memory effect.

Yet other patent literature relates to devices for endoscopic application of surgical staples adapted to attach surgical mesh to a body tissue.

An example of such a teaching is to be found in U.S. Pat. No. 5,364,004; U.S. Pat. No. 5,662,662; U.S. Pat. No. 5,634,584; U.S. Pat. No. 5,560,224; U.S. Pat. No. 5,588,581; and in U.S. Pat. No. 5,626,587.

There are a few patent and patent applications teaching the deployment of implants. For example U.S. Pat. No. 5,836,961 which relates to an apparatus used for developing an anatomic space for laparoscopic hernia repair and an implant for use therewith. The apparatus of U.S. Pat. No. 5,836,961 comprises a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

More patent literature can be found in PCT No. WO 08/065653 which relates to a device especially adapted to deploy an implant within a body cavity. The device is an elongate open-bored applicator and comprises (a) at least one inflatable contour-balloon, (b) at least one inflatable dissection balloon. The inflatable contour-balloon and the inflatable dissection balloon are adjustable and located at the distal portion. The elongate open-bored applicator additionally comprises (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

Although all the above described patents and patent applications demonstrate attachment means or deployment means, none of the literature found relates to a reversible connection device which enable a reversible coupling between the implant and the implant deployment device.

Thus, there is still a long felt need for a device that will enable a reversible connection between the implant and the implant deployment device.

SUMMARY

It is one object of the present invention to provide an active reversible connection mechanism adapted to provide a reversible attachment between a prosthetic implant and an implant deployment device, wherein said attachment can be actively reversed without requiring any application of force on said implant.

It is another object of the present invention to provide the active reversible connection mechanism as defined above, wherein said active reversible connection mechanism comprising at least one clip, hinge-like coupled to said implant deployment device, adapted to attach said implant to said implant deployment device: Said clip is characterized by having at least three configurations: (i) a horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate; such that (i) when said clip is in said horizontal configuration said attachment between said implant and said implant deployment device is obtained; (ii) when said clip is in said free motion configuration said detachment between said implant and said implant deployment device is obtained.

It is another object of the present invention to provide the active reversible connection mechanism as defined above, additionally comprising at least one locking bar characterized by at least two configurations: (i) lock configuration in which said lock bar maintains said clip in said horizontal configuration; and, (ii) free configuration in which said locking bar enables said clip a free movement.

It is another object of the present invention to provide the active reversible connection mechanism as defined above, wherein said active reversible connection additionally comprising at least one detachment actuator adapted to reversibly transform said locking bar from said lock configuration to said free configuration.

It is another object of the present invention to provide the active reversible connection mechanism as defined above, wherein said attachment between said implant and said implant deployment device is obtained once said locking bar is in its said lock configuration and said at least one clip is in said horizontal configuration such that the same at least partially penetrates said implant.

It is another object of the present invention to provide the active reversible connection mechanism as defined above, wherein said detachment is achieved by transforming said locking bar from said lock configuration to said free configuration via said at least one detachment actuator.

It is another object of the present invention to provide the active reversible connection mechanism as defined above, wherein said detachment actuator comprises a wire; further wherein said wire is attached to said lock bar.

It is another object of the present invention to provide the active reversible connection mechanism as defined above, wherein said transformation of said clip from said vertical configuration into their said horizontal configuration is performed manually by the physician or by the aid of a dedicated device.

It is another object of the present invention to provide a method for attaching a prosthetic implant to an implant deployment device. The method comprising steps selected inter alia from:

a. obtaining an active reversible connection mechanism adapted to provide a reversible attachment between said prosthetic implant and said implant deployment device; wherein said attachment can be actively revered without requiring any application of force on said implant; said active reversible connection comprising
  i. at least one clip, hinge-like coupled to said implant deployment device, adapted to attach said implant to said implant deployment device: Said clip is characterized by having at least three configurations: (i) horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate;
  ii. at least one locking bar characterized by at least two configurations: (i) lock configuration in which said lock bar maintains said clip in said horizontal configuration; and, (ii) free configuration in which said locking bar enables said clip a free movement; and,
b. providing said clips in said vertical configuration;
c. providing said locking bar in said lock configuration;
d. threading said implant through said clip;
e. transforming said clip into its said horizontal configuration thereby providing said attachment between said implant and said implant deployment device;

It is another object of the present invention to provide the method as defined above, additionally comprising step of providing said active reversible connection with at least one detachment actuator.

It is another object of the present invention to provide the method as defined above, additionally comprising step of reversibly transforming said locking bar from said lock configuration to said free configuration via said detachment actuator; thereby enabling free rotation of said clip such that detachment between said implant and said implant deployment device is obtained.

It is another object of the present invention to provide the method as defined above, additionally comprising step of introducing said implant deployment device into a body cavity.

It is another object of the present invention to provide the method as defined above, additionally comprising step detaching said implant from said implant deployment device.

It is another object of the present invention to provide the method as defined above, wherein said detachment additionally comprising steps of reversibly transforming said locking bar from said lock configuration to said free configuration via said detachment actuator; thereby enabling said clip to rotate freely such that said detachment between said implant and said implant deployment device is obtained.

It is another object of the present invention to provide a hernia kit useful in minimal invasive hernia surgery, comprising:
a. a implant;
b. implant deployment device, adapted to deploy said implant within the abdominal cavity; and,
c. an active reversible connection mechanism for reversible attaching said implant to said implant deployment device;
wherein attachment can be actively revered without requiring any application of force on said implant.

It is another object of the present invention to provide the hernia kit as defined above, wherein said active reversible connection mechanism comprising:
a. at least one clip, hinge-like coupled to said implant deployment device, adapted to attach said implant to said implant deployment device: Said clip is characterized by having at least three configurations: (i) horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate; such that (i) when said clip is in said horizontal configuration said attachment between said implant and said implant deployment device is obtained; (ii) when said clip is in said free motion configuration said detachment between said implant and said implant deployment device is obtained.

It is another object of the present invention to provide the hernia kit as defined above, additionally comprising at least one locking bar characterized by at least two configurations: (i) lock configuration in which said lock bar maintains said clip in said horizontal configuration; and, (ii) free configuration in which said locking bar enables said clip a free movement.

It is another object of the present invention to provide the hernia kit as defined above, wherein said active reversible connection additionally comprising at least one detachment actuator adapted to reversibly transform said locking bar from said lock configuration to said free configuration.

It is another object of the present invention to provide the hernia kit as defined above, wherein said attachment between said implant and said implant deployment device is obtained once said locking bar is in its said lock configuration and said at least one clip is in said horizontal configuration such that the same at least partially penetrates said implant.

It is another object of the present invention to provide the hernia kit as defined above, wherein said detachment is achieved by transforming said locking bar from said lock configuration to said free configuration via said at least one detachment actuator.

It is still an object of the present invention to provide the hernia kit as defined above, wherein said detachment actuator comprises a wire; further wherein said wire is attached to said lock bar.

It is an object of the present invention to provide the hernia kit as defined above, wherein said transformation of said clip from said vertical configuration into their said horizontal configuration is performed manually by the physician or by the aid of a dedicated device.

At least one aspect of this disclosure includes a system for closing an aperture in a biological tissue, comprising an implant deployment device including at least one frame arm and at least one clip operably disposed on said at least one frame arm, and a mesh attachment apparatus comprising at least one clip press, the at least one clip press comprising a body portion including at least one recess, and at least one chamfered press operably disposed in the at least one recess and configured to move between an extended position protruding at least partially from said recess and a retracted position, wherein the mesh attachment apparatus is configured to move the at least one clip from an open position to a closed position to facilitate loading an implant onto the implant deployment device.

In at least one aspect of the present disclosure, the mesh attachment apparatus further comprises a spring member disposed between said chamfered press and said body portion.

In at least one aspect of the present disclosure, the spring member biases the chamfered press toward the extended position.

In at least one aspect of the present disclosure, the chamfered press includes at least one chamfered surface and at least one press surface.

In at least one aspect of the present disclosure, the at least one chamfered surface includes a substantially linear chamfer.

In at least one aspect of the present disclosure, the at least one chamfered surface includes a substantially non-linear chamfer.

In at least one aspect of the present disclosure, a mesh attachment apparatus for use with an implant deployment device includes at least one clip press, the at least one clip press comprising, a body portion including at least one recess, and at least one chamfered press operably disposed in the at least one recess and configured to move between an extended position protruding at least partially from said recess and a retracted position, wherein the mesh attachment apparatus is configured to move the at least one clip from an open position to a closed position to facilitate loading an implant onto the implant deployment device.

In at least one aspect of the present disclosure, the mesh attachment apparatus further comprises a spring member disposed between said chamfered press and said body portion.

In at least one aspect of the present disclosure, the spring member biases the chamfered press towards the extended position.

In at least one aspect of the present disclosure, the chamfered press includes at least one chamfered surface and at least one press surface.

In at least one aspect of the present disclosure, the at least one chamfered surface includes a substantially linear chamfer.

In at least one aspect of the present disclosure, the at least one chamfered surface includes a substantially non-linear chamfer.

In at least one aspect of the present disclosure, method includes providing a mesh attachment apparatus for use with an implant deployment device, comprising at least one clip press, the at least one clip press comprising a body portion including at least one recess, and at least one chamfered press operably disposed in the at least one recess and configured to move between an extended position protruding at least partially from said recess and a refracted position, wherein the mesh attachment apparatus is configured to move the at least one clip from an open position to a closed position to facilitate loading an implant onto the implant deployment device.

In at least one aspect of the present disclosure, the mesh attachment apparatus further comprises a spring member disposed between said chamfered press and said body portion.

In at least one aspect of the present disclosure, the spring member biases the chamfered press towards the extended position.

In at least one aspect of the present disclosure, the chamfered press includes at least one chamfered surface and at least one press surface.

In at least one aspect of the present disclosure, the at least one chamfered surface includes a substantially linear chamfer.

In at least one aspect of the present disclosure, the at least one chamfered surface includes a substantially non-linear chamfer.

In at least one aspect of the present disclosure, the method further includes using the mesh attachment apparatus to move at least one clip of an implant deployment device from an open position to a closed position.

In at least one aspect of the present disclosure, the method further includes using the mesh attachment apparatus to releasably attach a surgical implant to at least one clip of an implant deployment device by compressing the implant onto the at least one clip in an open position and allowing the at least one chamfered surface move the at least one clip from the open position to a closed position.

BRIEF DESCRIPTION OF THE DRAWINGS

The invention is herein described, by way of example only, with reference to the accompanying drawings, wherein:

FIG. 10 is a perspective view of the clip press of FIG. 6;

FIG. 11 is another cross-sectional view of the clip press of FIG. 6;

FIG. 12 is another cross-sectional view of the clip press of FIG. 6;

FIG. 24 illustrates an implant deployment device in accordance with the present disclosure, with an implant releasably connected thereto; and FIG. 25 is an enlarged view of the clips as shown in FIG. 24, in a closed position.

DETAIL DESCRIPTION OF THE SPECIFIC EMBODIMENTS

Figure 1A:
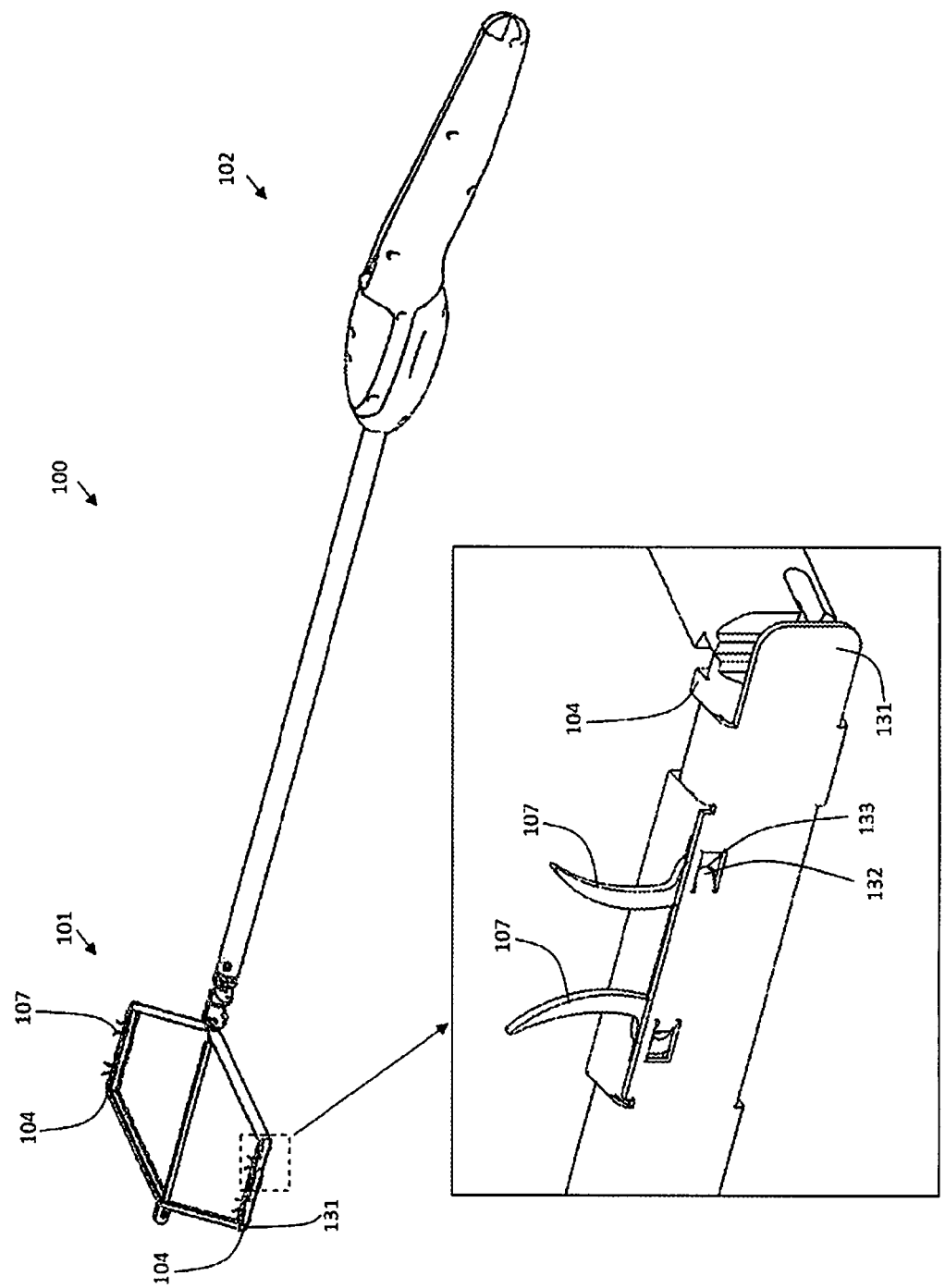
FIG. 1A illustrates an example of a implant deployment device which comprises said active reversible connection mechanism.

The following description is provided, alongside all chapters of the present invention, so as to enable any person skilled in the art to make use of the invention and sets forth the best modes contemplated by the inventor of carrying out this invention. Various modifications, however, is adapted to remain apparent to those skilled in the art, since the generic principles of the present invention have been defined specifically to provides means and method for creating a reversible and active connection between a implant and a implant deployment device.

The present invention provides an active reversible connection mechanism between a prosthetic implant and an implant deployment device wherein said connection can be performed during a surgery at a standard surgery room by the medical staff.

Furthermore, the present invention provides means so as to enable the surgeon to actively eliminate said attachment once detachment between said implant deployment device and said implant is necessary.

It should be emphasized that some of the major advantages of the present invention, with respect to the prior art, is to provide a fast and intuitive method for creating a reliable connection between an implant and an implant deployment device in the surgery room. Embodiments of an implant include, but are not limited to, a surgical patch, a surgical mesh, or other biocompatible implants usable in repairing a defect in body tissue.

In addition, the present invention provides means to actively disconnect said implant from said implant deployment device, when said disconnection is desired without the need to exert large forces on said implant and/or said tissue.

The term "Hernia" refers hereinafter for umbilical hernia, hiatal hernia, ventral hernia, postoperative hernia, epigastric hernia, spiegelian hernia, inguinal hernia and femoral hernia, generally any abdominal wall related hernia.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components.

The term "hinge like connection" can refer to a standard hinge or to a living hinge (i.e., a thin flexible hinge (flexure bearing) made from plastic that joins two rigid parts together while allowing them to bend along the line of the hinge).

The term "controlled deployment" refers hereinafter to an implant deployment which is continuous; i.e., the deployment is not binary but analogous—there are several deployment levels. This is in contrast so conventional deployment system is now days (see for example U.S. Pat. No. 5,370,650), in which the deployment of the implant relies upon the elasticity of a loop member surrounding the implant such that the implant can be either fully folded or fully unfolded. No intermediate are enabled. In the present invention, there can be several deployment stages.

The term "bidirectional" or "fully reversible deployment" refers hereinafter to the deployment of the implant, which according to the present invention, is fully reversible. In other words, the implant deployment is bidirectional, i.e., the implant can be fully folded (i.e., deployed within the body) and then, if the surgeon desires, the implant can be fully unfolded simply by the reconfiguration of the flexible arms from the initial stage to the final stage and vice versa.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "articulation" refers hereinafter to a joint or juncture between two segments of the device. The articulating means of the present invention provides the ability to better adjust the device to the curvature of the treated tissue.

The term "orientation" refers hereinafter to the rotation of the mesh within the abdominal cavity so as to fit to the hernia. Usually the mesh is not symmetric in shape (i.e., rectangular or i.e., ellipse)—therefore it has different directions. By rotating the mesh within the abdominal cavity—one can decide which direction is turned where.

The term "adjusting" refers hereinafter to rolling, folding, and winding of the implant, thus preparing and enabling the insertion of said implant into the abdominal cavity.

The term "active reversible connection" refers hereinafter to a coupling between the implant and the implant deployment device implant deployment device in which the coupling/decoupling between the implant and the implant deployment device is enabled by an act performed by the user (namely the physician). Once said User performed said act, said coupling/decoupling is canceled.

According to the present invention the coupling/decoupling is obtained actively via the aid of dedicated clips which are characterized by at least two configurations:
 (a) substantially horizontal/parallel configuration (in which an attachment between the implant and the implant deployment device is provided);
 (b) substantially vertical configuration; and,
 (c) a configuration in which the clips are free to rotate.

Before explaining the figures, it should be understood that the invention is not limited in its application to the details of construction and the arrangement of the components set forth in the following description or illustrated in the drawings. The invention can be carried out in various ways.

Reference is now being made to FIG. 1A illustrates an example of an implant deployment device 100 which comprises said active reversible connection mechanism.

Implant deployment device 100 is defined hereinafter as a surgical device which can introduce a implant into a body cavity of a patient; implant deployment device 100 can deploy said implant such that it is at least partially spared inside the body cavity; alternatively implant deployment device 100 can only introduce said implant into the body cavity without performing any deployment.

In general, implant deployment device 100 comprises at least two portions: a distal portion 101 and a proximal portion 102. The proximal portion is adapted to remain outside the body, adjacently to the user and the distal portion 101 is adapted to be inserted into the body.

The distal portion comprises at least one frame arm 104 to which the implant is attached. Each frame arm 104 comprises said active reversible connection mechanism which provides reversible attachment between each frame arm 104 and the implant 106 such that said implant can be rolled/folded on said distal portion 101, and inserted into the patient's body cavity through a laparoscopic cannula or a small incision.

It should be noted that the term reversible refers hereinafter to the ability to both attach the implant to the implant deployment device and to decouple the same from the implant deployment device.

Said active reversible connection mechanism comprises at least one clip 107. Said clip is coupled to said frame arm 104 by hinge tab 132. Said active reversible connection is covered by cover 131 which is attached to the frame arm 104. Cover 131 comprises at least one hinge tab 132 which is adapted to hold said clip 107 attached to frame arm 104 an to serve as a hinge allowing free rotation of said clip 107. Said hinge tab 132 is inserted through hinge hole 133, located at clip 107 and through hole 134, located at frame arm 104.

Reference is now being made to FIGS. 2A-2D which illustrate the internal operation of said active reversible connection mechanism. For the purpose of illustration only, cover 131 is removed from these drawings.

A locking bar 203 is located inside groove 204 at frame arm 104. Said locking bar 203 can move linearly inside said groove 204 and comprises at least one groove 205. Said locking bar 203 is characterized by at least two positions: free position, in which each of said groove/s 205 is substantially located below said clip 107 (see FIGS. 2C and 2D), and lock position, in which said groove 205 is located away from said clip 107 (see FIGS. 2A and 2B).

In the lock position of the locking bar 203, the clip 107 are substantially perpendicular to the frame arm 104; and in free position of the locking bar 203, the clip 107 are free to rotate (hence, as will be discussed hereinafter a detachment is enabled).

A disconnection wire 206 is attached to said locking bar 203. Said wire 206 can be pulled proximally to the proximal portion 102 and is adapted to transform said locking bar 203 from its said lock position into its said free position.

According to this embodiment, each clip 107 comprises at least 3 sections: protruding portion (PP) 201 adapted to protrude through said implant during said connection process, hinge hole 133, and locking tab 202 which is tilted toward frame arm 104.

Figure 2A:
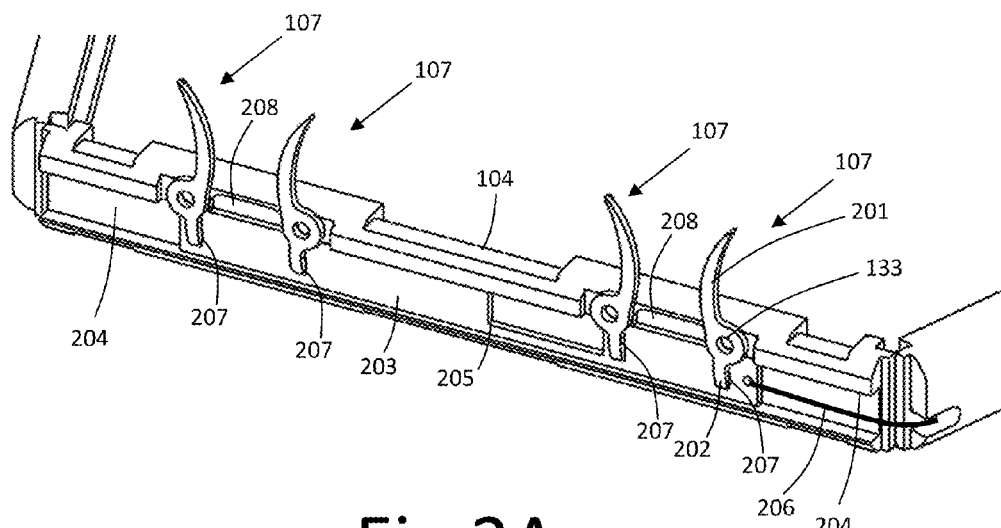
FIGS. 2A-2D illustrate the internal operation of said active reversible connection mechanism.
Figure 2B:
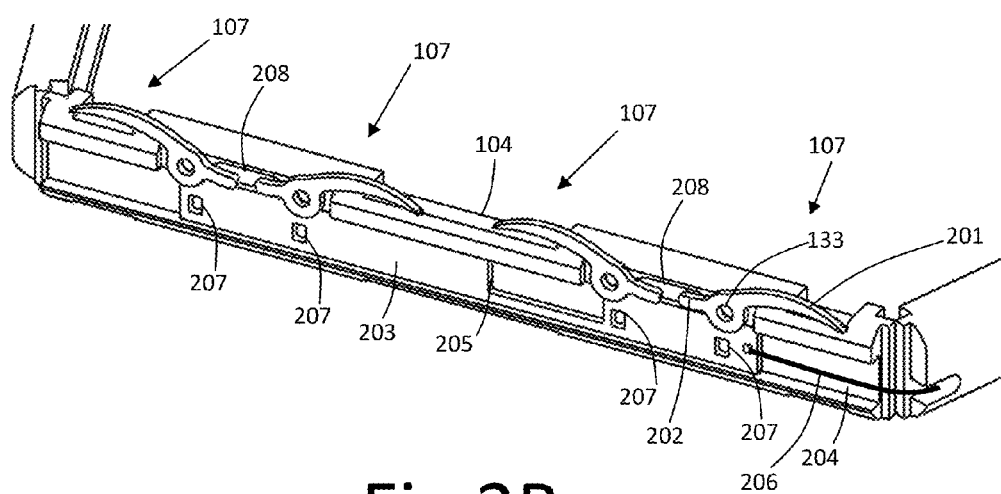
Figure 2C:
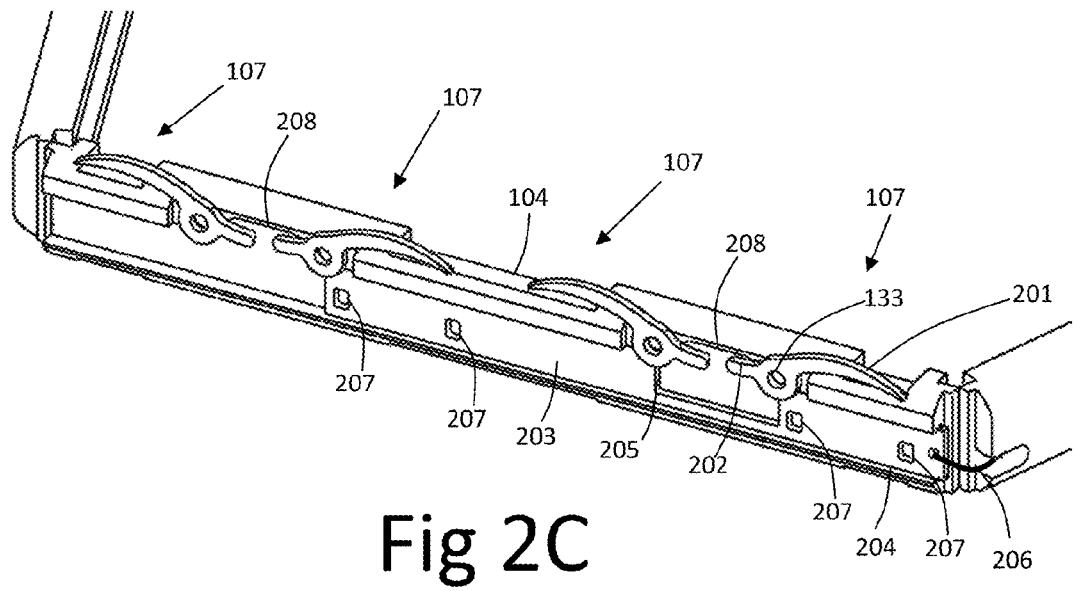
Figure 2D:
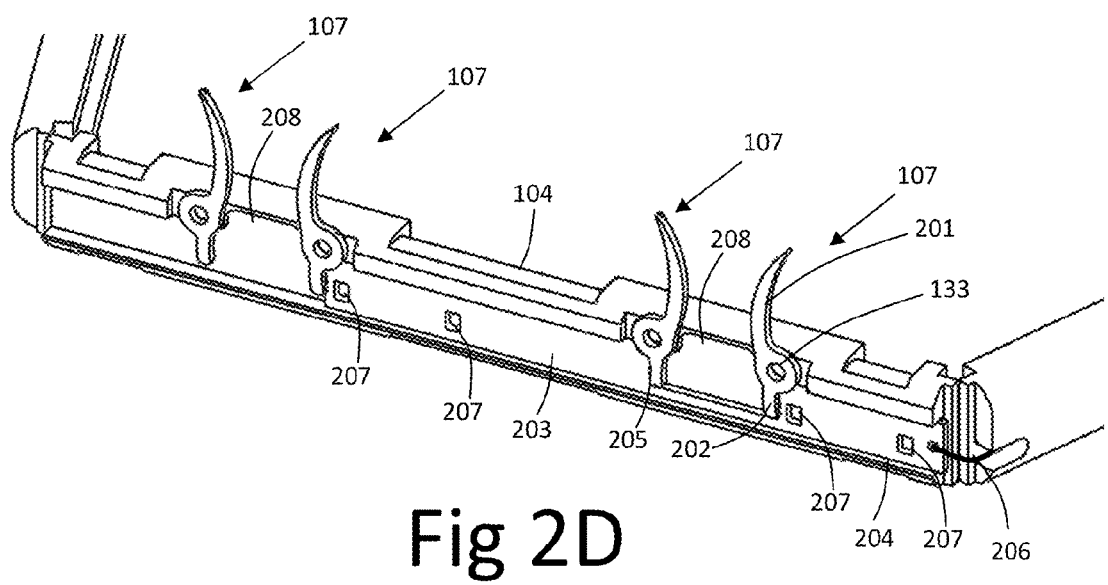

Each of said clip 107 is characterized by at least two configurations: horizontal/parallel configuration in which said clip 107 is substantially horizontal and parallel to said frame arm 104 (FIGS. 2B, 2C) and vertical configuration in which said clip 107 is substantially vertical with respect to said frame arm 104 (FIGS. 2A and 2D).

At least one holding hole 207 is located at said locking bar 203 and is adapted to hold said clip 107 in its vertical configuration.

At least one niche 208 in located at frame arm 104 adapted to accommodate said locking tab 202 of said clip 107 while the last is in its said horizontal/parallel configuration.

Reference is now being made to FIGS. 3A-3D illustrating a method of using said active reversible connection mechanism in order to provide said reversible connection between said implant and said implant deployment device 100. Again, for the purpose of illustration only, cover 131 was removed from these drawings.

Figure 3A:
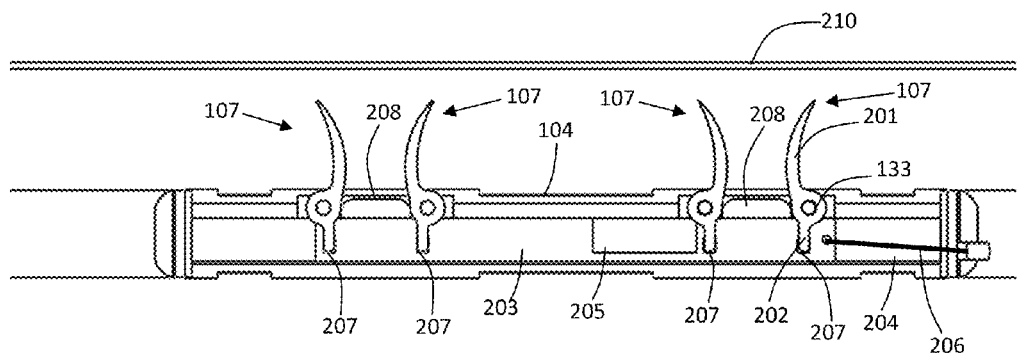
FIGS. 3A-3E illustrate a method of using said active reversible connection mechanism for providing said reversible connection between said implant and said implant deployment device.

FIG. 3A illustrates the initial state of said active reversible connection mechanism in which all of said clip 107 are in their vertical configuration and said locking bar 203 is positioned in said lock position.

Figure 3B:
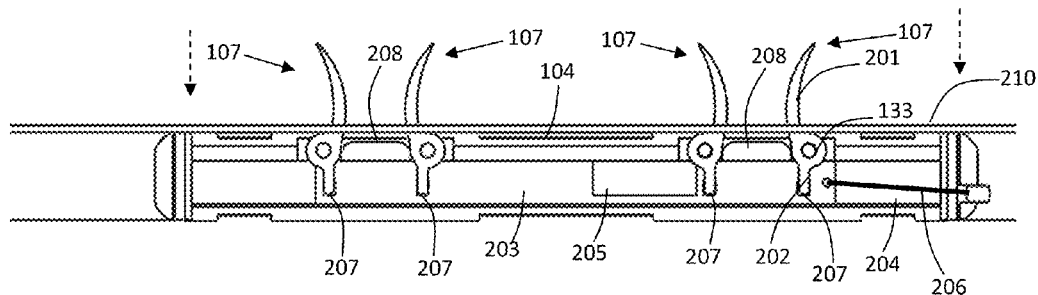

As can be seen in the figure, said locking tab 202 of each said clip 107 is located inside said holding hole 207, therefore each clip 107 is held in its said vertical configuration and can penetrate a implant 210 whilst the last is mounted on top of said implant deployment device (see FIG. 3B).

Figure 3C:
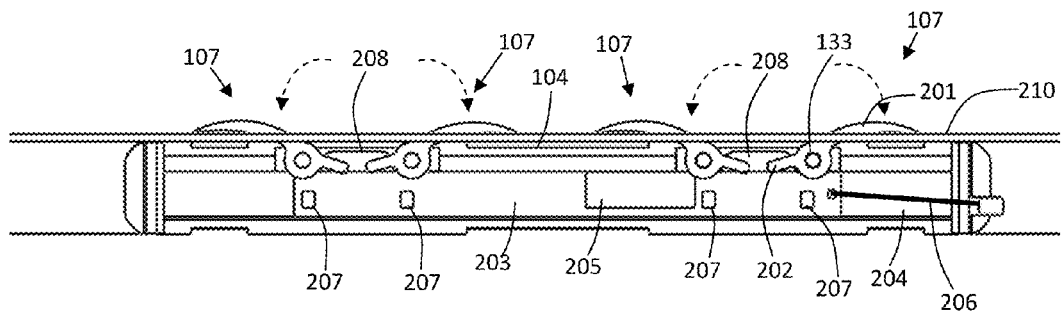

Once said implant is mounted, each of said clip 107 is transformed from said vertical configuration into their said horizontal configuration (see FIG. 3C).

Said transformation can be achieved either manually (i.e., the physician will manually rotate the clips 107 thereby transforming them from said vertical configuration into their said horizontal configuration) or by the aid of a dedicated device.

Once said clip 107 is transformed to its horizontal configuration while said locking bar is in its said lock position, said locking tab 202 is sprigged into niche 208. Since the locking tab 202 is titled inwardly, if said clip 107 is pulled upwardly in this state, the locking tab 202 is stooped by the upper edge of said locking bar 203, therefore, the rotation back to said vertical configuration of said clip 107 is limited by said locking bar 203 and said clips 107 are locked in said horizontal configuration, holding said implant attached to said frame arm 104.

It should be pointed out that it is a unidirectional mechanism. In other words, if one tries to force clips 107 to its vertical configuration, locking tabs 202 will bump into locking bar 203.

Figure 3D:
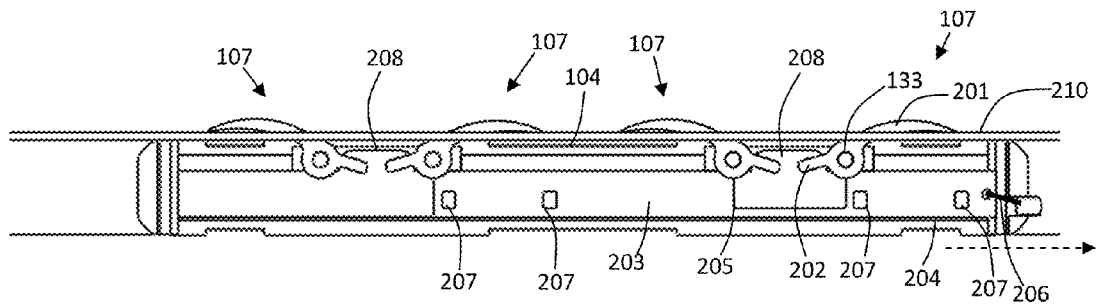
Figure 3E:
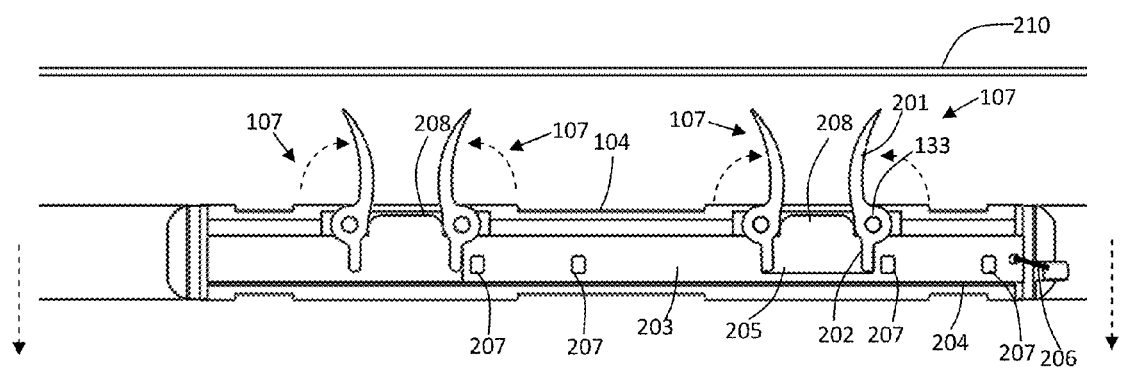

By further pulling said locking bar 203 towards the proximal portion the clips 107 are unlocked and can be rotated be back to its vertical configuration (see FIGS. 3D and 3E).

Once detachment between said implant 210 and said implant deployment device in desired, locking bar 203 is pulled backward by wire 206, changing the position of said locking bar form its said lock position into its said free position (see FIG. 3D). In said free position of the locking bar 203, the clips 107 are free to rotate (hence, as will be discussed hereinafter, a detachment between the implant deployment device and the implant is enabled).

Once locking bar 203 is positioned in said free position, said groove's 205 is located below said clips 107, therefore said locking bar 202 is no longer limiting the movement of said clips 107 enabling their free movement. In this state, detachment can be obtained by simply pulling said frame arm 104 away from said implant; as a result, said clips 107 rotate back into their said vertical configuration and are released from said implant (see FIG. 2E).

Reference is now made to FIG. 4A-4H, which illustrate an embodiment of a stapling or mesh attachment apparatus 400 adapted for providing said reversible connection by said active reversible connection mechanism. Said mesh attachment apparatus 400 comprises a frame 401 which holds the distal portion 101 of an implant deployment device 100. Four staplers 403 are connected to the frame 401 at each corner by four separate hinges (either standard or living hinges). Each said stapler 403 is adapted to push down the implant 210 through a pair of clip 107 and to transform said clips 107 from a vertical position into a horizontal position (thus providing said reversible connection). Staple or clip presses 404 are located at the end of each stapler inside groove 405 and adapted to push clip 107 into horizontal position. Each pair of staplers 403 is connected via bridge 407 in order to prevent lateral movement of said staplers 403 during the stapling process. A snap groove 406 is located at the center of the frame 401 and adapted to reversibly hold said implant deployment device 100 attached to stapling or mesh attachment apparatus 400 until said reversible attachment is obtained.

Figure 4A:
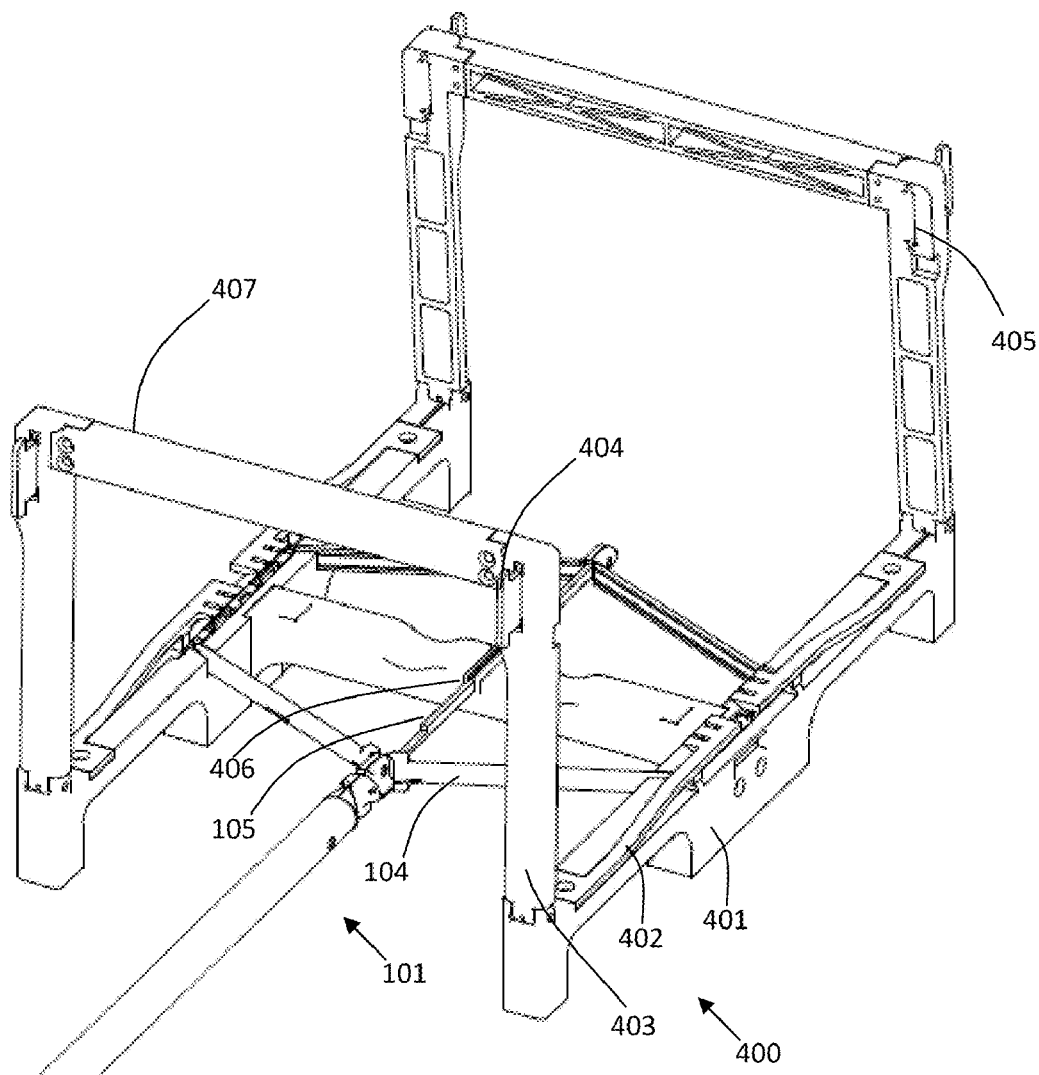
FIGS. 4A-4H illustrate an embodiment of a stapling or mesh attachment apparatus adapted for providing a reversible connection by the active reversible connection mechanism.
Figure 4B:
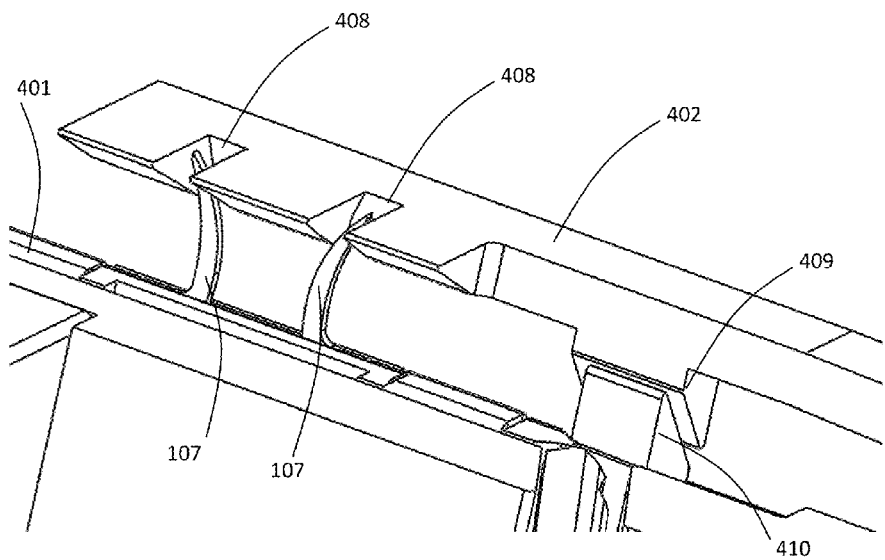
Figure 4C:
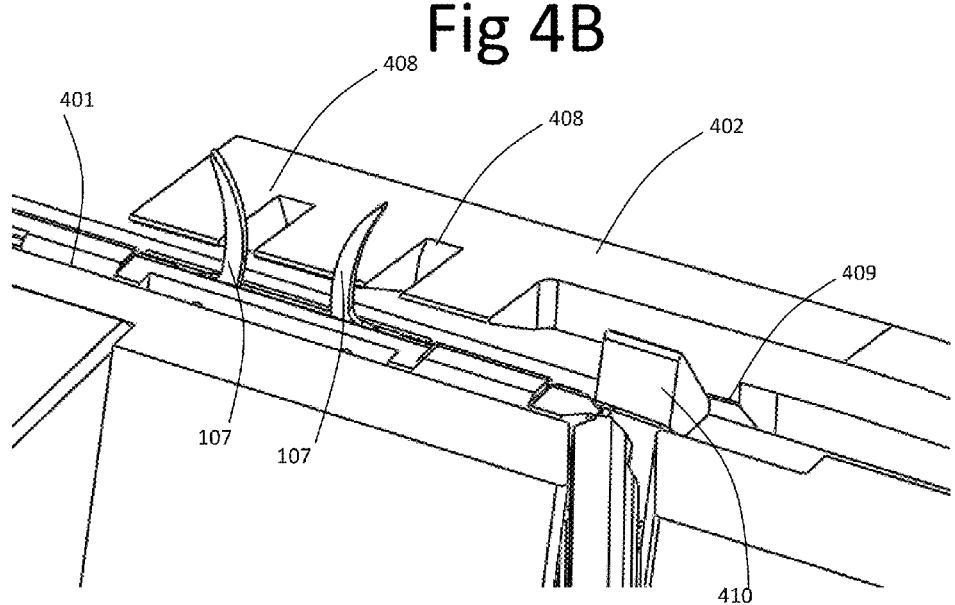
Figure 4D:
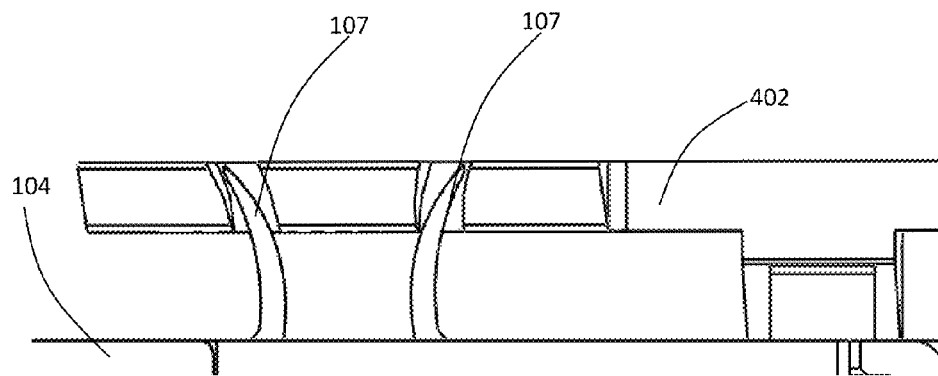
Figure 4E:
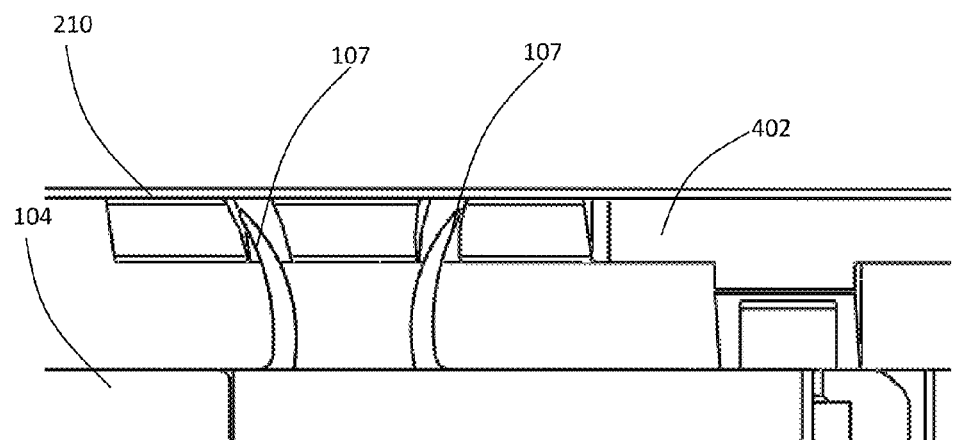

Each pair of clip 107 is held in a vertical position by clip holder 402. Each said clip holder 402 is adapted to hold a pair of clip 107 in vertical position in order to allow its insertion through the implant 210 during the stapling process. In addition, clip holder 402 is adapted the hold the clips vertical during shipment in order to allow stapling in the operation room without the need of any preparation. As illustrated in FIGS. 4B-4C, each clip holder 402 comprises two grooves 408 which hold the clip 107 in a vertical position. Once stapling process is preformed and the surgeon is lowering the stapler 403 toward the implant, each clip holder 402 is pushed down and as a result it is also moving laterally. In this state, since the clip 107 are extracted from groves 408, their transformation from vertical into horizontal position is enabled; said lateral movement of said clip holder 402 is obtained as bulge 409 at clip holder 402 is sliding along bulge 410 at the stapling frame 401 during the down movement of clip holder 402.

Figure 4F:
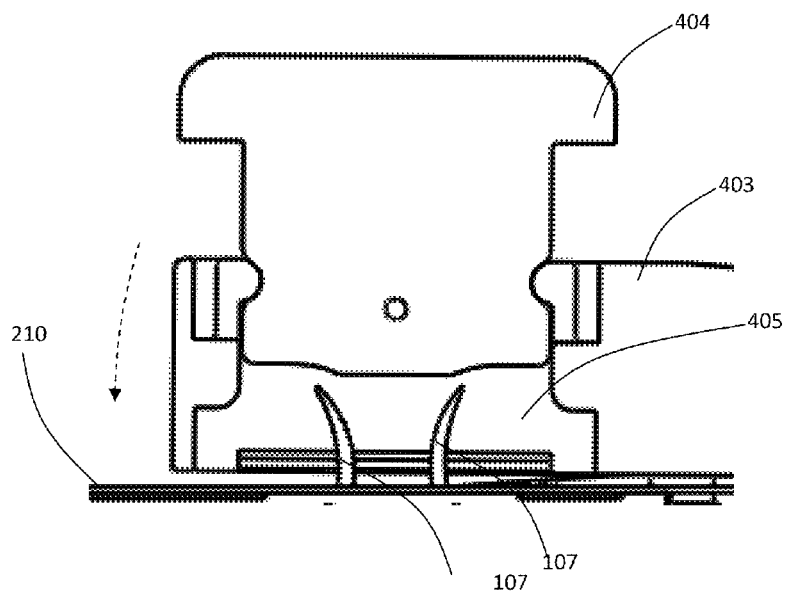

FIGS. 4D-4G illustrate the process of connecting the implant 210 to one pair of clip. At the initial stage (FIG. 4D), the clips are held vertically by clip holder 402. Next, an implant 210 is places on top of the stapling apparatus (FIG. 4E); the stapler 403 is then lowered toward the implant 210 by the surgeon (or other member of the medical staff); as a result the two clip 107 are penetrating through implant 210 and into groove 405 (FIG. 4F). During the initial penetration, clip 107 is held by clip holder 402, thus premature transformation from vertical into horizontal position is prevented. Once the clip 107 are completely inserted into said implant 210, clip holder 402 is positioned laterally relative to the clip 107 (as also described is FIGS. 4B-4C); at this stage the surgeon pushes on stapler press 404 and lowers it toward clip 107 (FIG. 4G), as a result clip 107 position is transformed form vertical position into horizontal position. Since the said lock bar 203 is located at its said lock position, once clip 107 are substantially horizontal position, they are locked in this stage, thus providing said reversible connection between implant 210 and implant deployment device 100. Once said connection is obtain with all clip 107, implant deployment device is removed from SA 400.

Figure 4G:
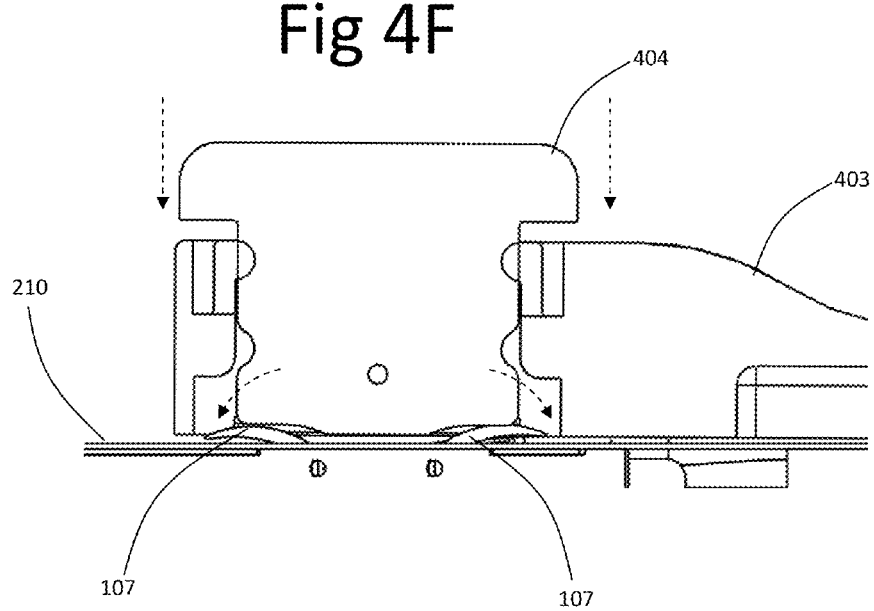

Referring now to FIG. 4G1-4G3, another embodiment of a clip press 704 is shown transitioning from a first configuration wherein the clips 107 are substantially vertical (FIG. 4G1), through a second configuration wherein the clips 107 are at a point between the vertical position and a close position (FIG. 4G2), to a third configuration wherein clips 107 are in the closed position (FIG. 4G3). Clip press 704 will be described in more detail hereinbelow.

Figure 4H:
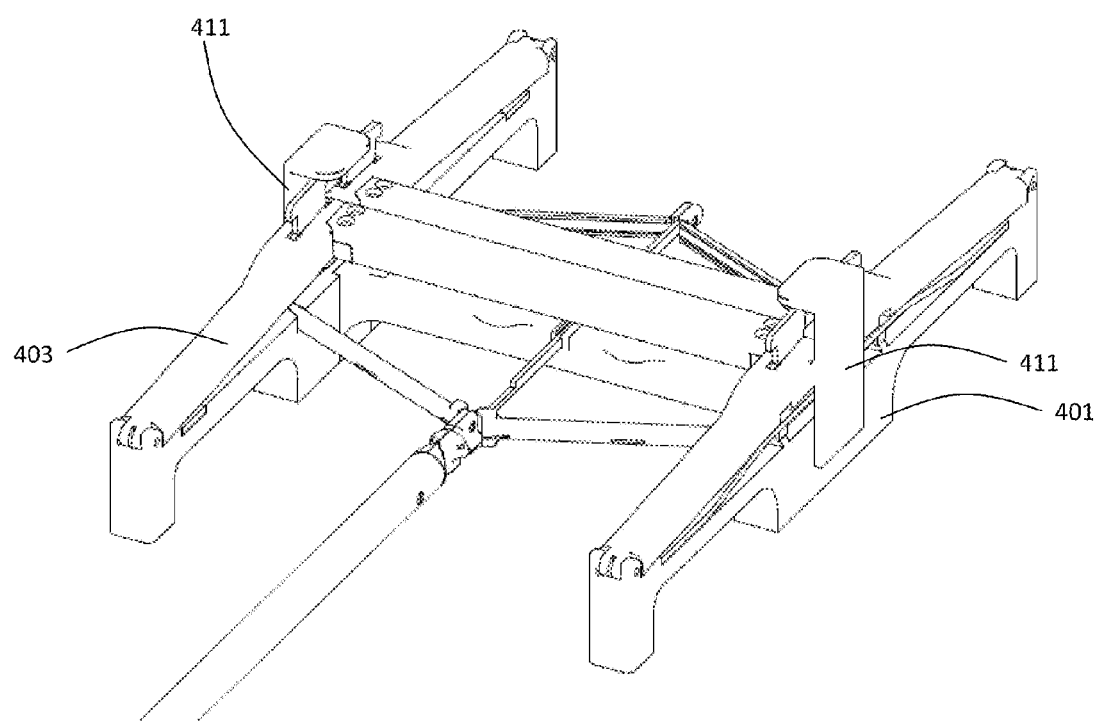

FIG. 4H illustrates the configuration of stapling apparatus 400 during shipment. In order to reduce package volume during shipment and to keep the device ready for stapling, at least one, preferably two, packaging caps 411 are utilized. Said caps 411 are reversibly attached to the frame 401, and adapted to retain stapler 403 in a substantially horizontal position during device shipment. In addition, said caps 411 also prevent down movement of stapler press 404, prevent lateral movement of clip holder 402 and prevent non-deliberate extraction of implant deployment device 100 from frame 401.

Once the device in removed from its packaging during the surgery, said pack caps 411 are removed by the medical staff in order to allow stapling of the implant 210 to the implant deployment device 100. Once the caps 411 are removed, the staplers 403 springs into horizontal position allowing the placement of implant 210 onto the stapling apparatus 400 and implant deployment device 100.

In order to allow tight spreading of the implant 210 during surgery, said stapling process is preformed while implant deployment device 100 is not completely opened; as a result, once implant deployment device is completely opened inside the abdominal cavity, it is stretched beyond its original dimension (as was during stapling) therefore tight spreading is obtained.

Figure 5:
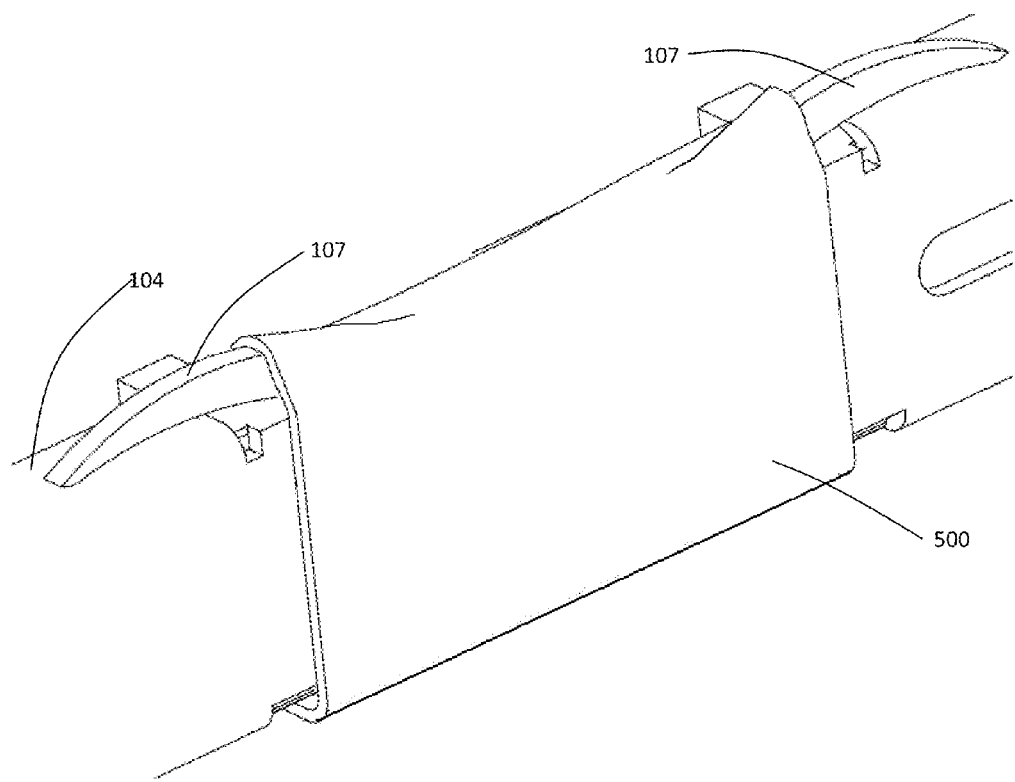
FIG. 5 illustrates an embodiment of a staple return spring.
Figure 6:
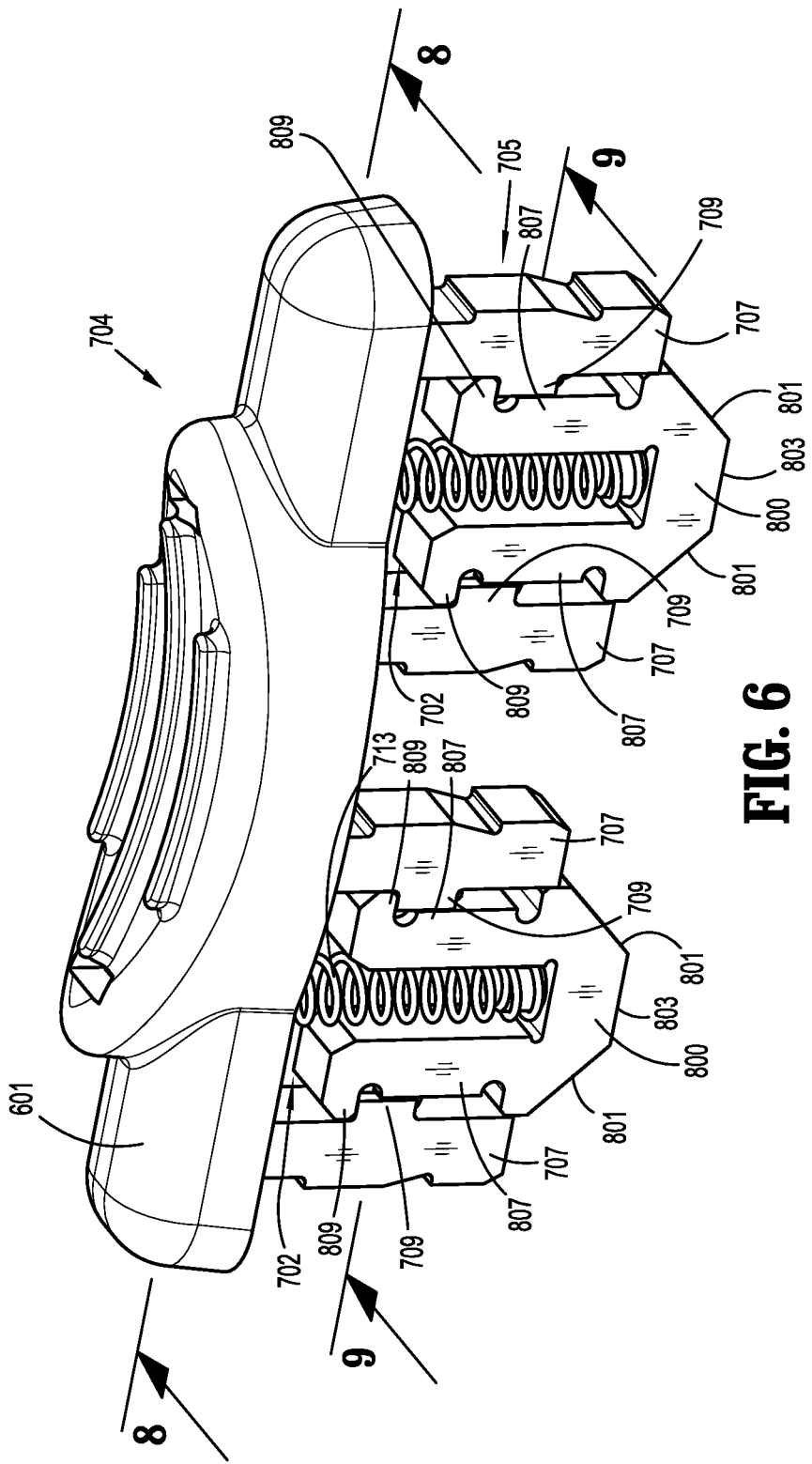
FIG. 6 illustrates an embodiment of a clip press in accordance with the present disclosure.
Figure 7:
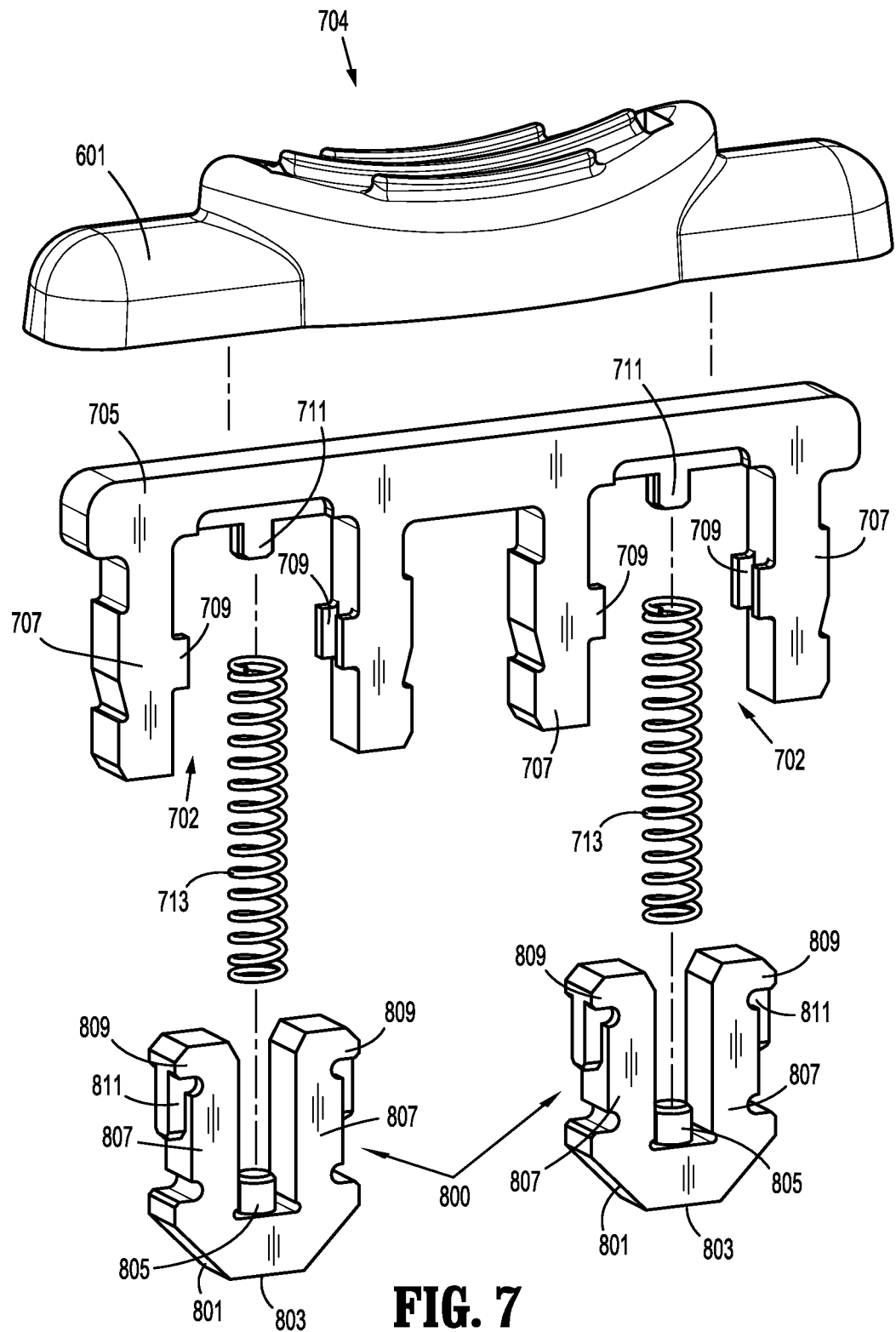
FIG. 7 is an exploded view of the clip press of FIG. 6.
Figure 8:
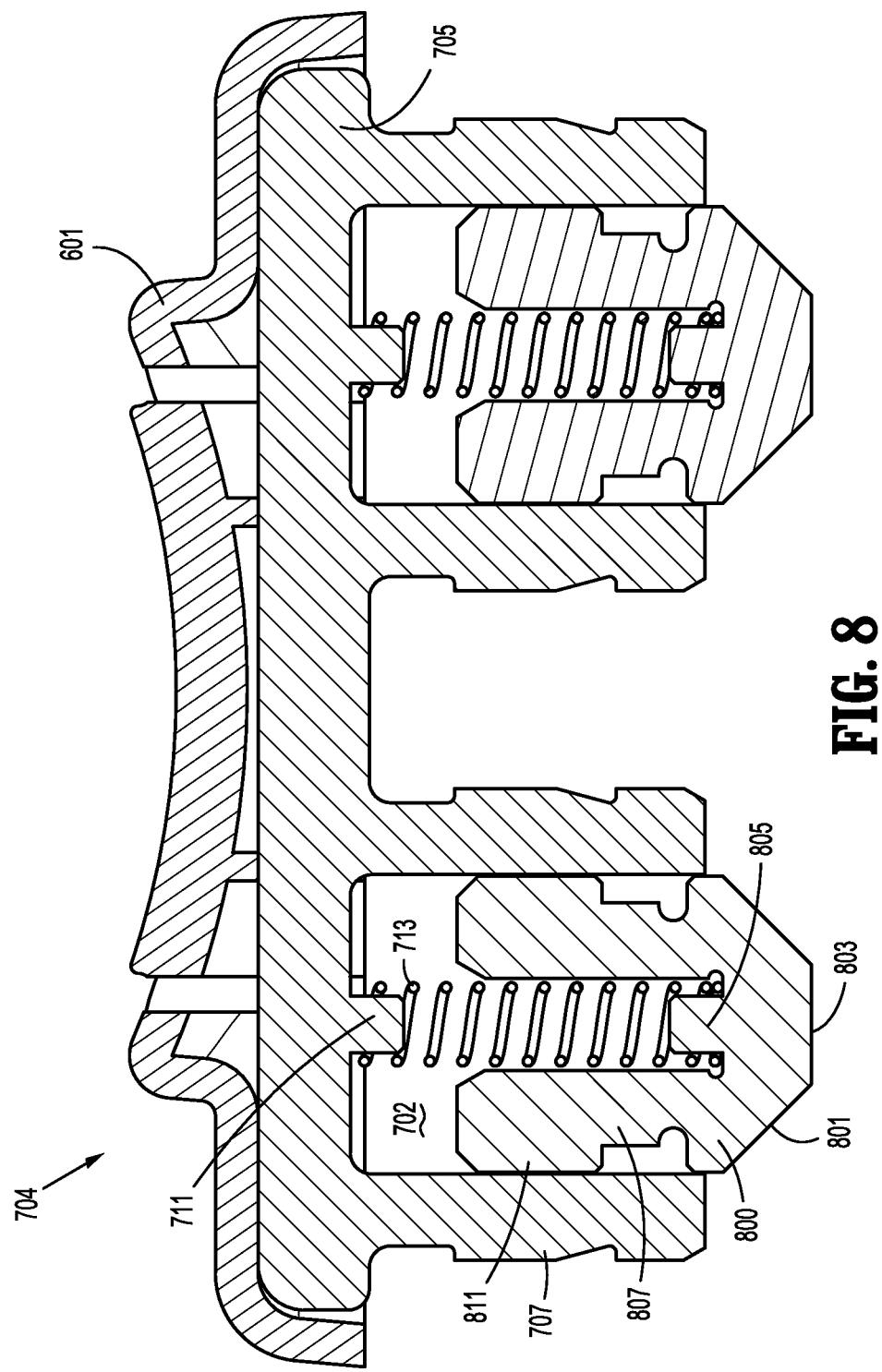
FIG. 8 is a cross-sectional view of the clip press of FIG. 6.
Figure 9:
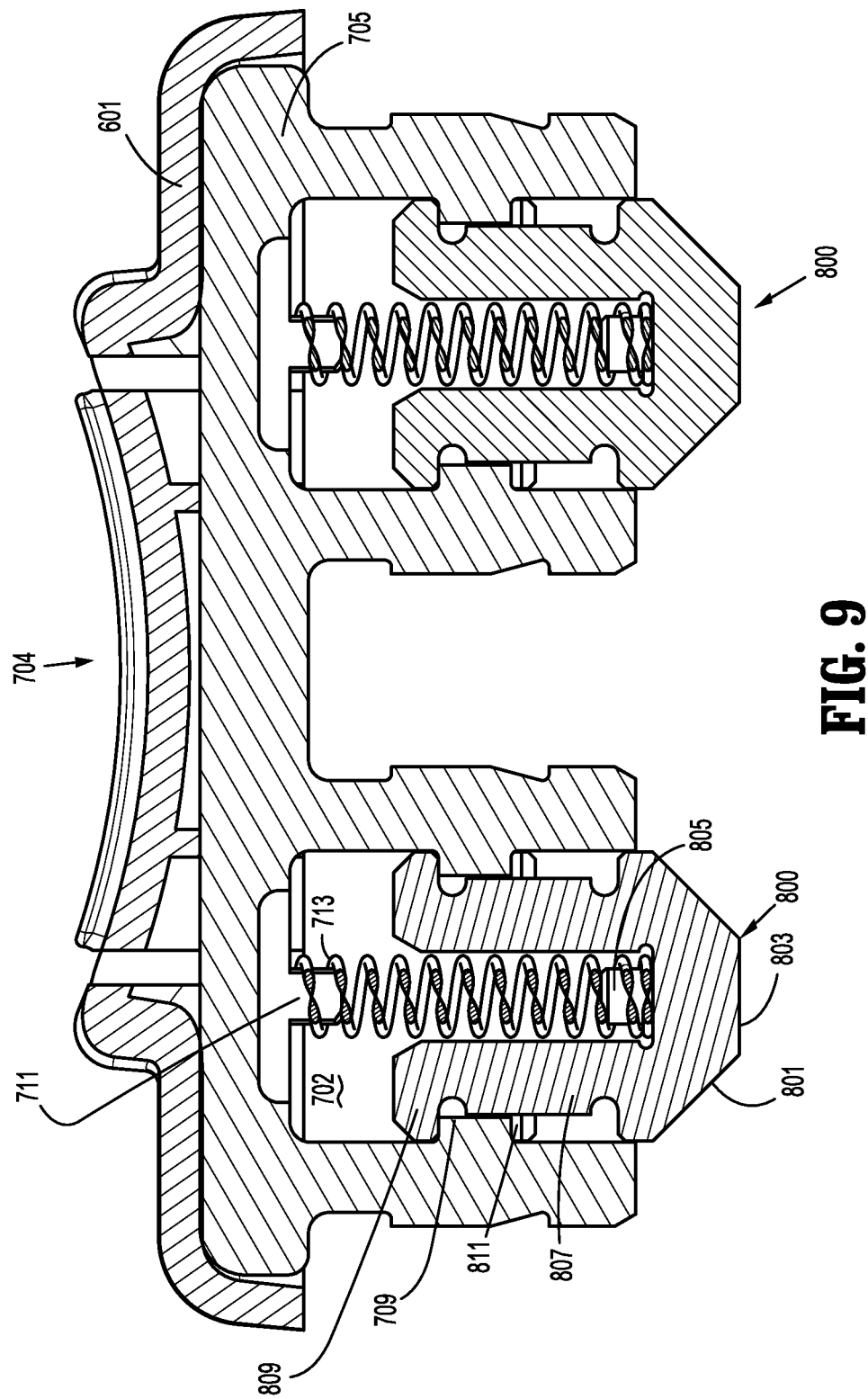
FIG. 9 is another cross-sectional view of the clip press of FIG. 6.

Reference is now being made to FIG. 5 which illustrates an embodiment of a staple return spring 500. In general, staple return spring 500 is needed in order to return clip 107 into horizontal position immediate after detachment from the implant 210; this is necessary in order prevent damage to internal organs by the sharp tip of clip 107 and in order to prevent clip 107 from being caught at the trocar or at the tissue during device extraction.

Referring to FIGS. 6-12, an embodiment of a clip press 704 is shown. Clip press 704 includes a body portion 705. Optionally, a cap 601 may be disposed on body portion 705. Body portion 705 may include legs 707 defining at least one recess 702 in the body portion 705. Legs 707 may include one or more protrusions 709 extending into the recess 702.

The clip press 704 further includes at least one chamfered press 800 operably disposed in the recess 702 and configured to move between an extended position (FIG. 4G1 and FIG. 6) protruding at least partially from the recess 702 and a retracted position (FIG. 4G3).

Chamfered press 800 includes at least one chamfered surface 801 and at least one press surface 803. Chamfered surface 801 may be substantially linear as shown in the figures. Alternatively, one or more chamfered surfaces 801 of a chamfered press 800 may have a non-linear shape. Press surface 803 may be flat or any other suitable shape.

Chamfered press 800 has arms 807 extending from chamfered surfaces 801. Arms 807 may include stop 809. Stop 809 may interact with protrusions 709 on the legs 707 of the body portion 705 to define how far chamfered press 800 extends from the recess 702 of body portion 705.

Chamfered press 800 may also include a guide member 811 that extends from arms 807 and slides between the protrusions 709 on legs 707.

A spring member 713 may be disposed between the body portion 705 and the chamfered press 800 such that the spring member 713 biases the chamfered press 800 toward the extended position. As such, the chamfered press 800 may include a spring post 805 for releasably attaching the spring member 713 to the chamfered press 800. The body portion 705 may also have a body spring post 711 for connecting the spring member 713 to the body portion 705 as well as the chamfered press 800. When the chamfered press 800 is moved to a retracted position (FIG. 4G3), the spring member 713 compressed and provides an increased spring force in the opposite direction. If the chamfered press 800 is not being blocked, the spring member 713 pushes the chamfered press 800 back to the extended position (FIG. 7A).

With continued reference to FIGS. 6-12 and with further reference to FIGS. 13-23, a system as herein described is shown having at least one clip press 704 disposed on a press arm 901 of mesh attachment apparatus 900, an implant 999, and an implant deployment device 100.

In FIGS. 13-17, the mesh attachment apparatus 900 is shown in isolation from the implant 999 and the implant deployment device 100. Mesh attachment apparatus 900 differs from the previously shown stapling apparatus 400 in FIG. 4A in that mesh attachment apparatus 900 only has one press arm 901 as opposed to the two shown in FIG. 4A. It is important to note that while clip press 704 is shown in figures as configured to function with the mesh attachment apparatus 900 as shown in FIGS. 13-23, one of ordinary skill in the art would appreciate that it is possible to split clip press 704 such that there is a single chamfered press 800, or even a multiple of chamfered presses 800, such that clip press 704 is configured to be used with other embodiments of mesh attachment apparatuses as shown herein or otherwise. Mesh attachment apparatus 900 further includes base frame 903 that is configured to receive an implant deployment device 100. Press arm 901 may be hingedly connected to base frame 903 to allow press arm 901 to fold over base frame 903 and align clip press 704 over the clips 107 of the implant deployment device 100 when implant deployment device 100 is disposed on the base frame 903. Clip press 704 is configured to move the clips 107 from an open position toward a closed position. As herein described with respect to this and other embodiments, an open position is any position where the clips 107 as herein described are not in contact with or close proximity to the frame arm 104, and a closed position is where the clips 107 are in contact with or close proximity to the frame arm 104 to clamp an implant.

Figure 13:
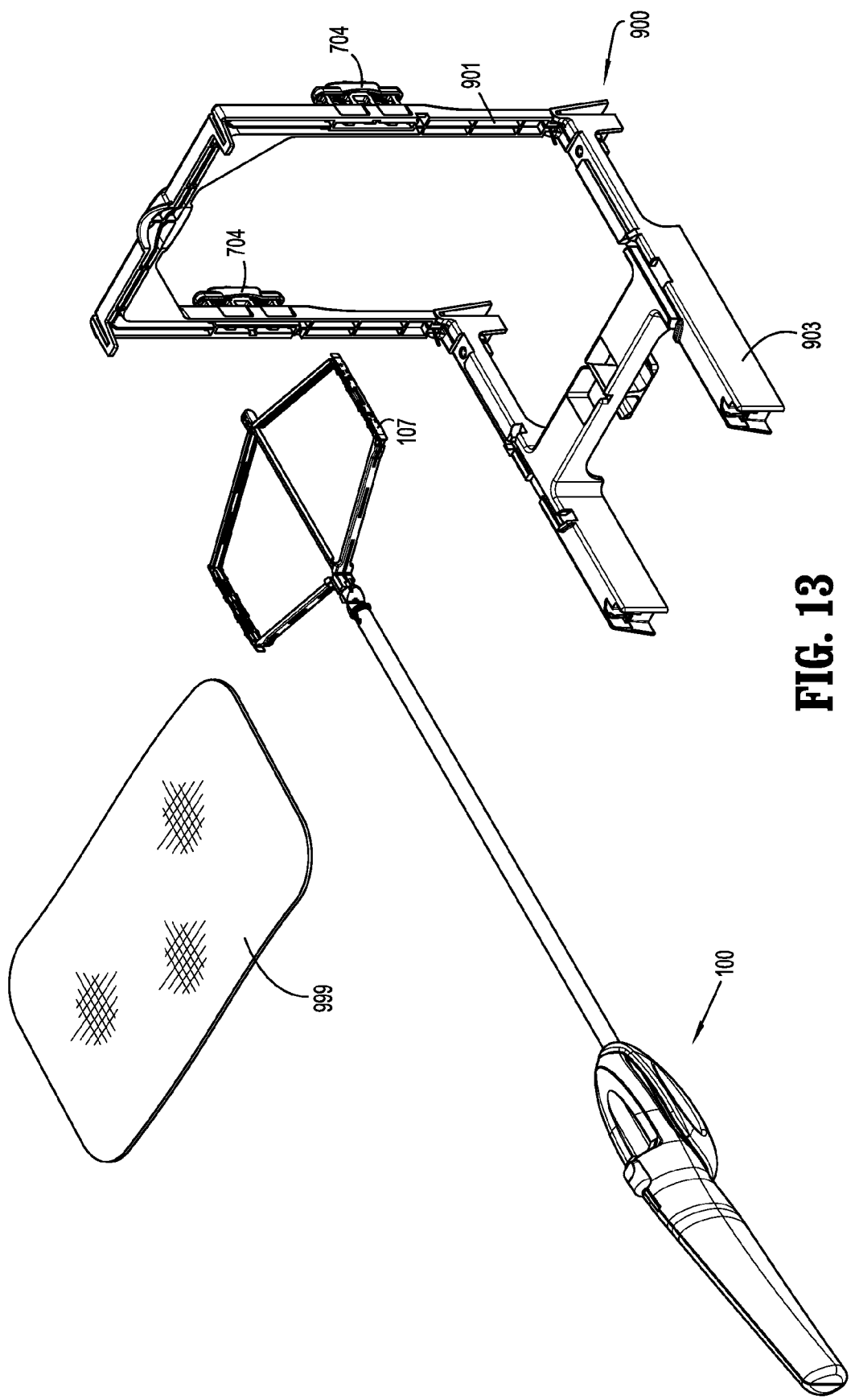
FIG. 13 illustrates an embodiment of a system for closing an aperture in a biological tissue in accordance with the present disclosure.
Figure 14:
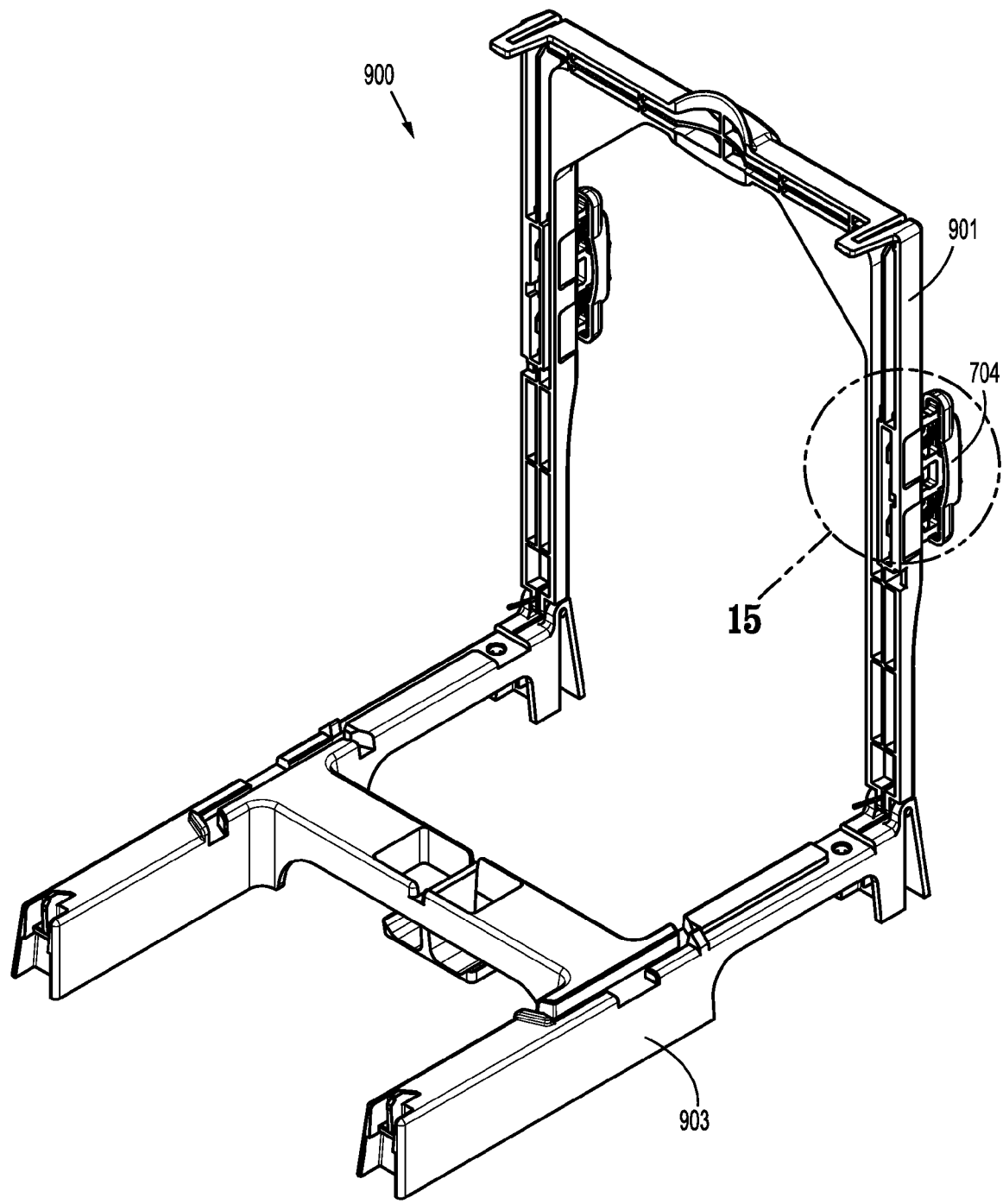
FIG. 14 illustrates an embodiment of a mesh attachment apparatus in accordance with the present disclosure.
Figure 15:
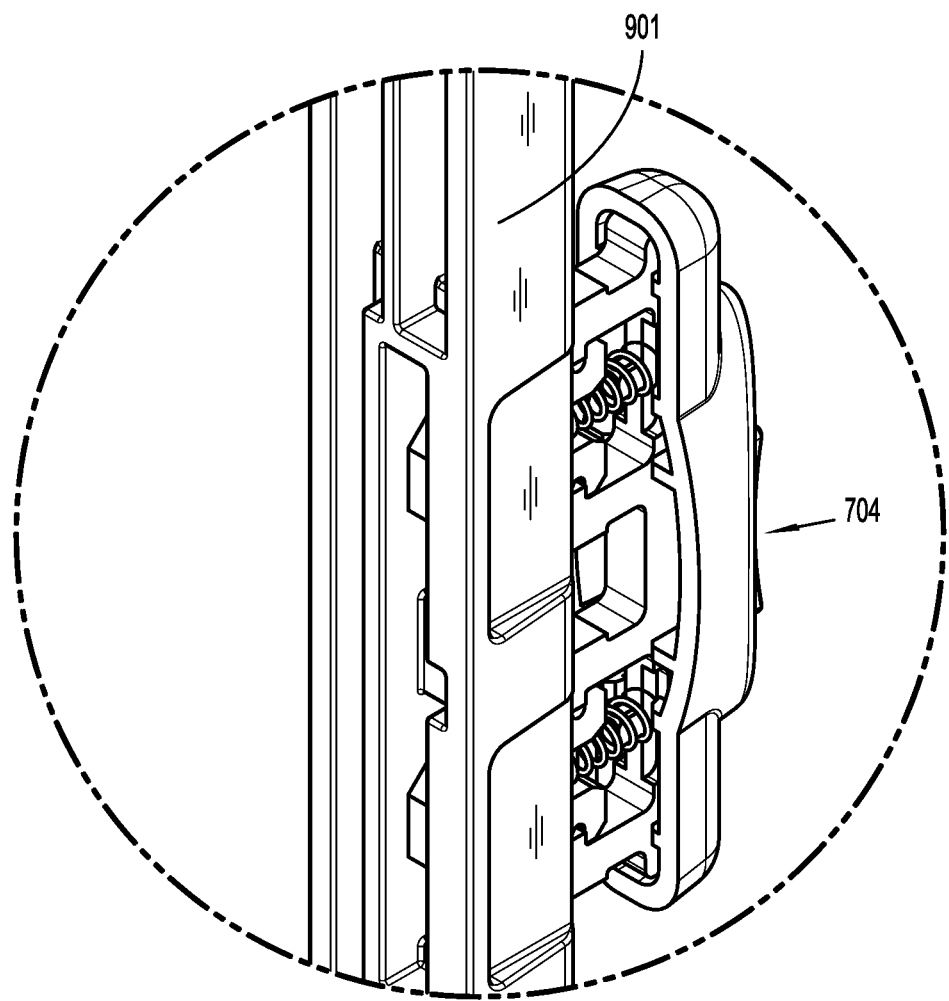
FIG. 15 is an enlarged view of the area of detail identified in FIG. 14.
Figure 16:
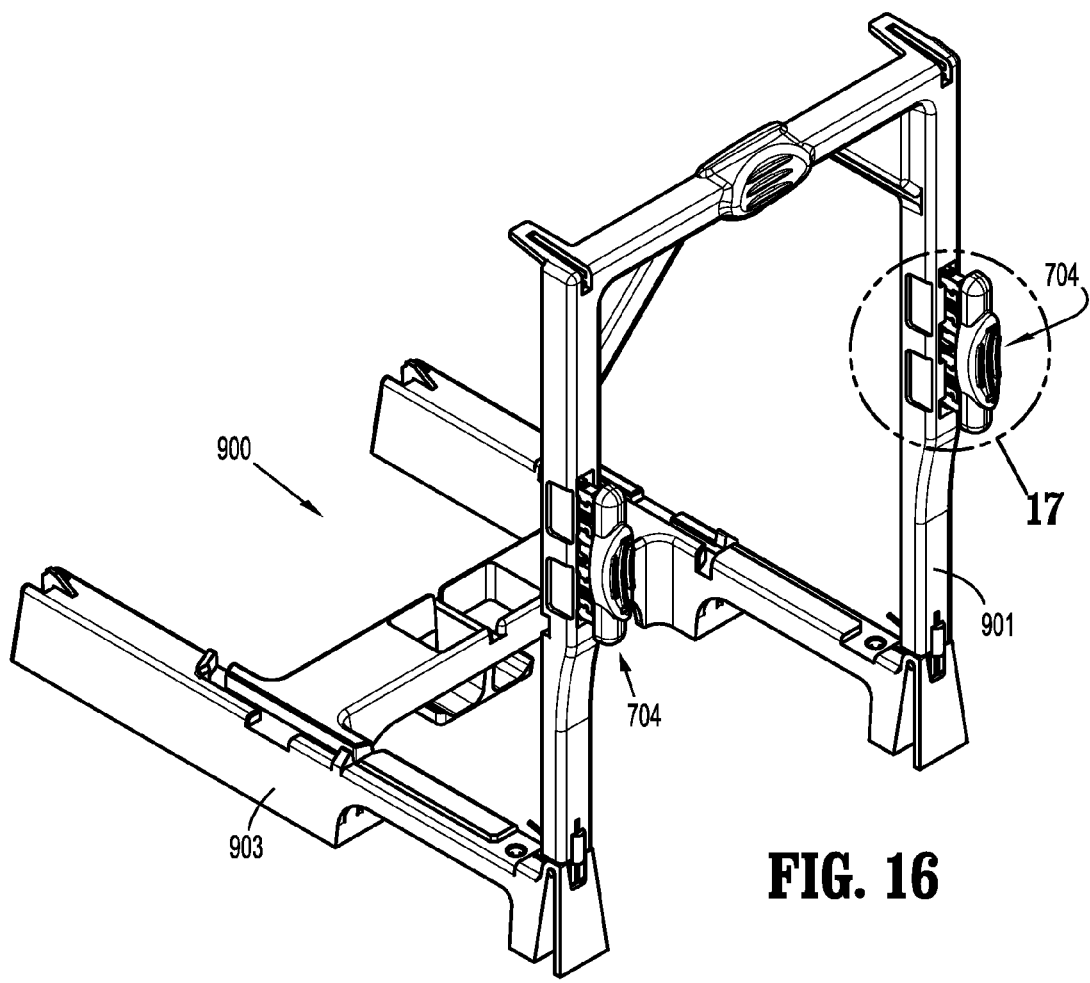
FIG. 16 illustrates an embodiment of a mesh attachment apparatus in accordance with the present disclosure.
Figure 17:
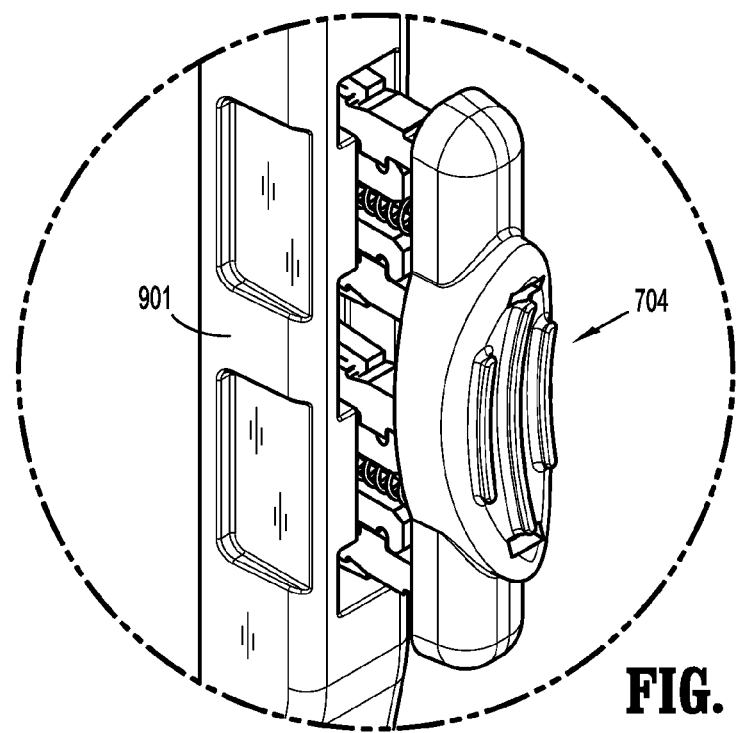
FIG. 17 is an enlarged view of the area of detail identified in FIG. 16.
Figure 18:
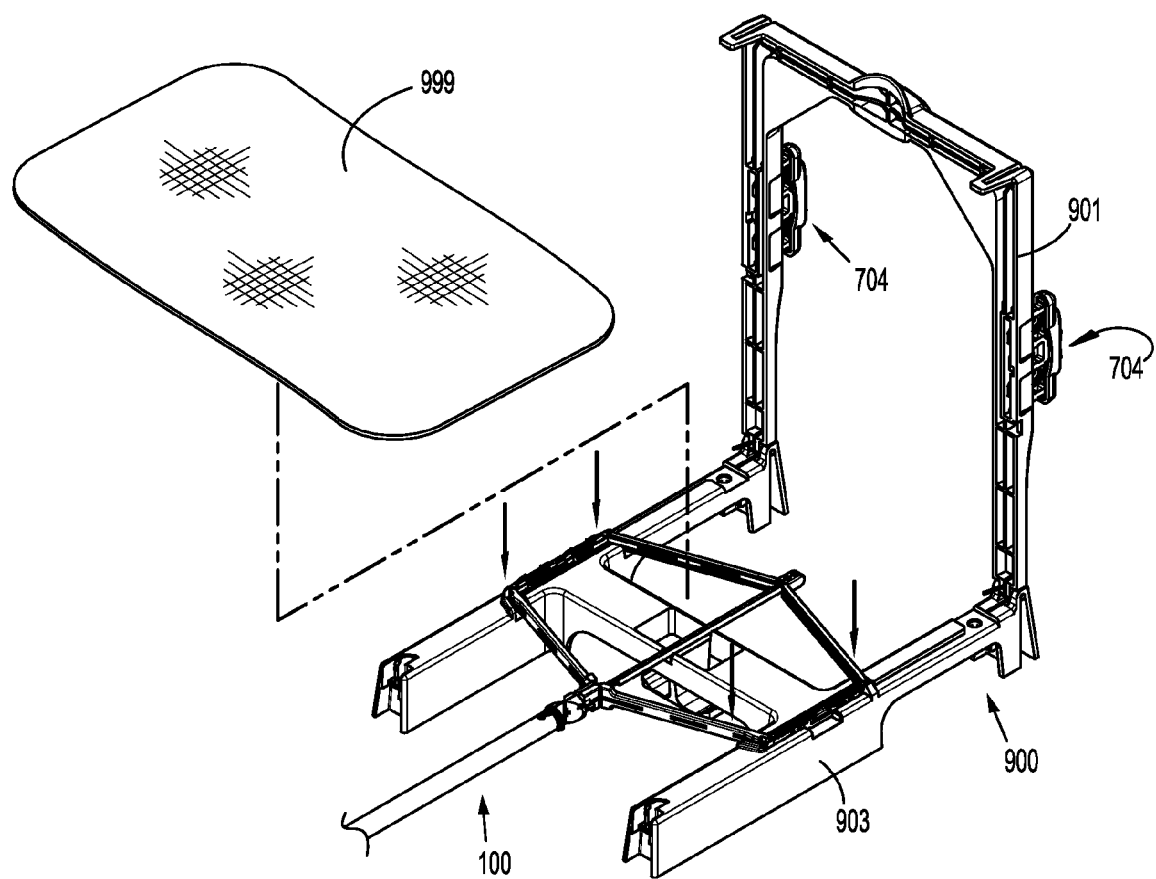
FIG. 18 illustrates an embodiment of a system for closing an aperture in a biological tissue in accordance with the present disclosure, in an open configuration.
Figure 19:
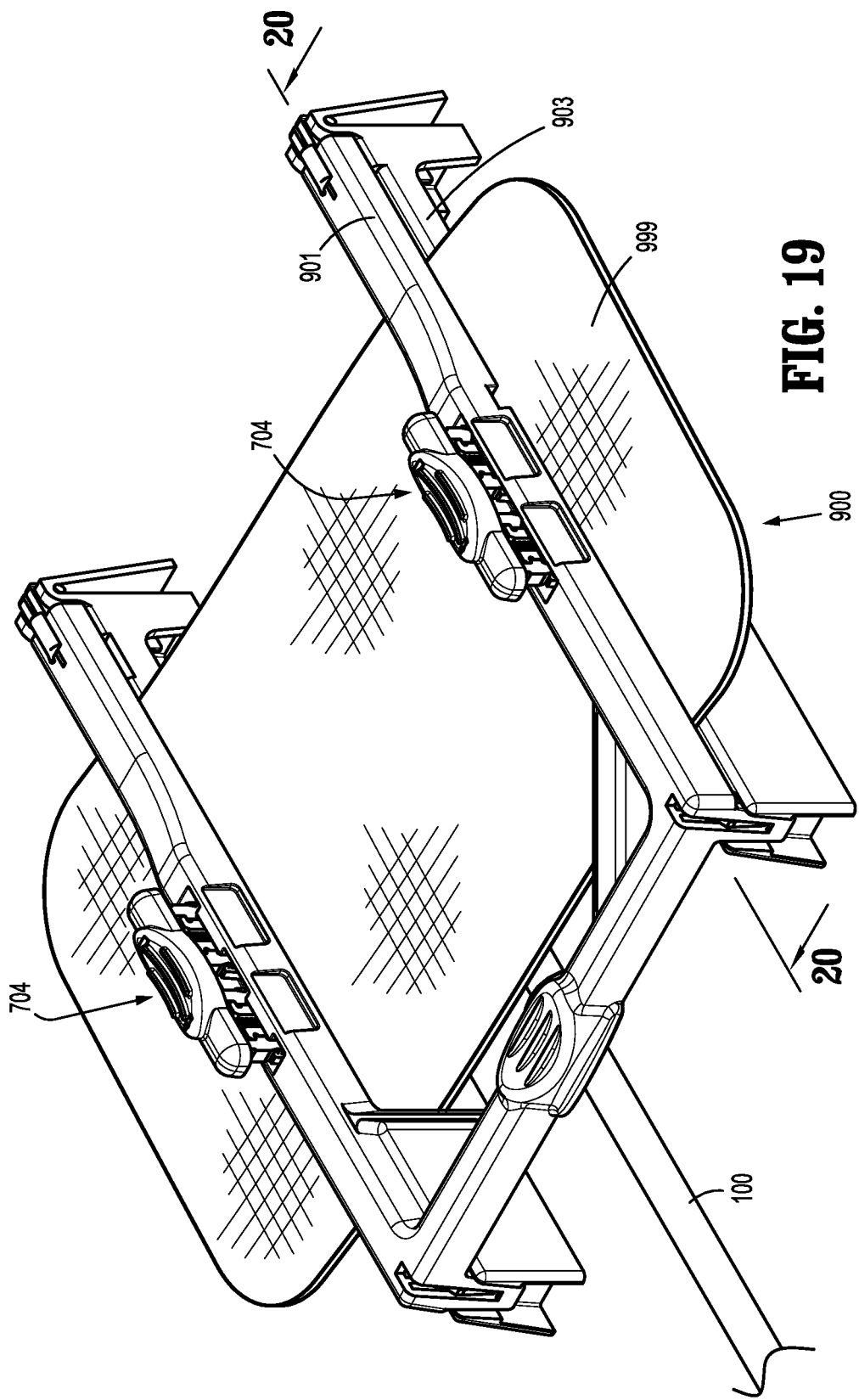
FIG. 19 illustrates an embodiment of a system for closing an aperture in a biological tissue in accordance with the present disclosure, in a closed configuration.

Referring specifically to FIGS. 18-23, the process of attaching an implant 999 to an implant deployment device 100 using clip press 704 and mesh attachment apparatus 900 is shown. In FIG. 13, the implant deployment device 100 is shown disposed in base frame 903 and implant 999 is shown before being placed on top of the implant deployment device 100. Once the implant 999 is disposed on the implant deployment device 100, press arm 901 is placed over the implant 999 in a closed position, as shown in FIG. 19.

Figure 20:
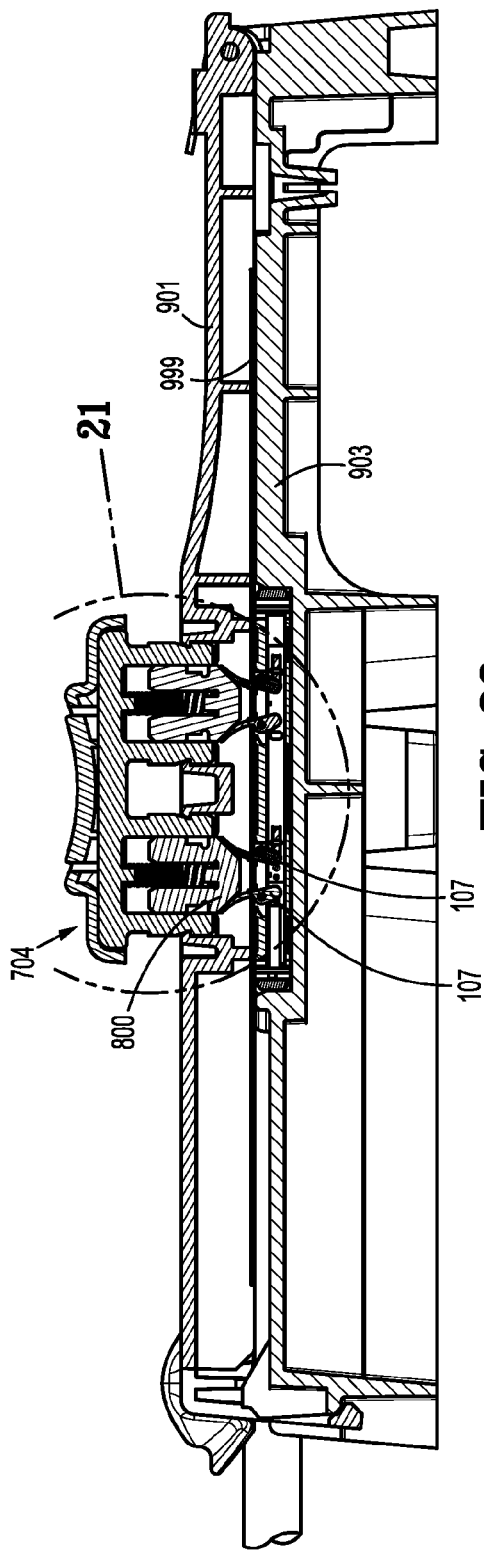
FIG. 20 is a side cross-sectional view of the mesh attachment apparatus of FIG. 19 showing a clip press in a first position.
Figure 21:
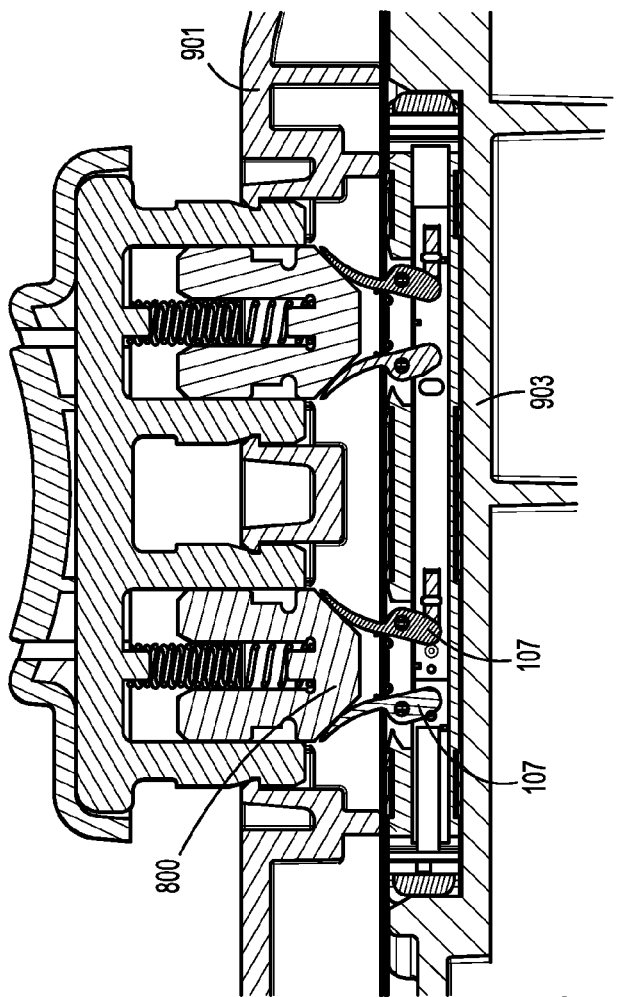
FIG. 21 is an enlarged view of the area of detail of FIG. 20.

Referring to FIGS. 20 and 21, the press arm 901 is placed over the implant 999 such that the clip press 704 is aligned with the clips 107 as shown. The implant 999 is pierced by the clips 107. The clip press 704 contacts the clips 107 at the chamfered surface 801 of the chamfered press 800 while the clips 107 are in the open position, but does not substantially move the clips 107 until the chamfered press 800 is pushed down by a user.

The clip press 704 is advanced toward the frame arm 104 and the base frame 903, and the chamfered surfaces 801 push clips 107 toward the closed position without the chamfered press 800 substantially moving toward the retracted position. If the force required to rotate the clips 107 is less than the force required to compress the spring member 713, than the chamfered press 800 will not move toward the retracted position at all while in a position between that shown in FIGS. 21 and 22. As shown, the clips 107 are urged to smoothly rotate by the chamfered surfaces 801 as the chamfered press 800 is advanced toward the frame arm 104.

Figure 22:
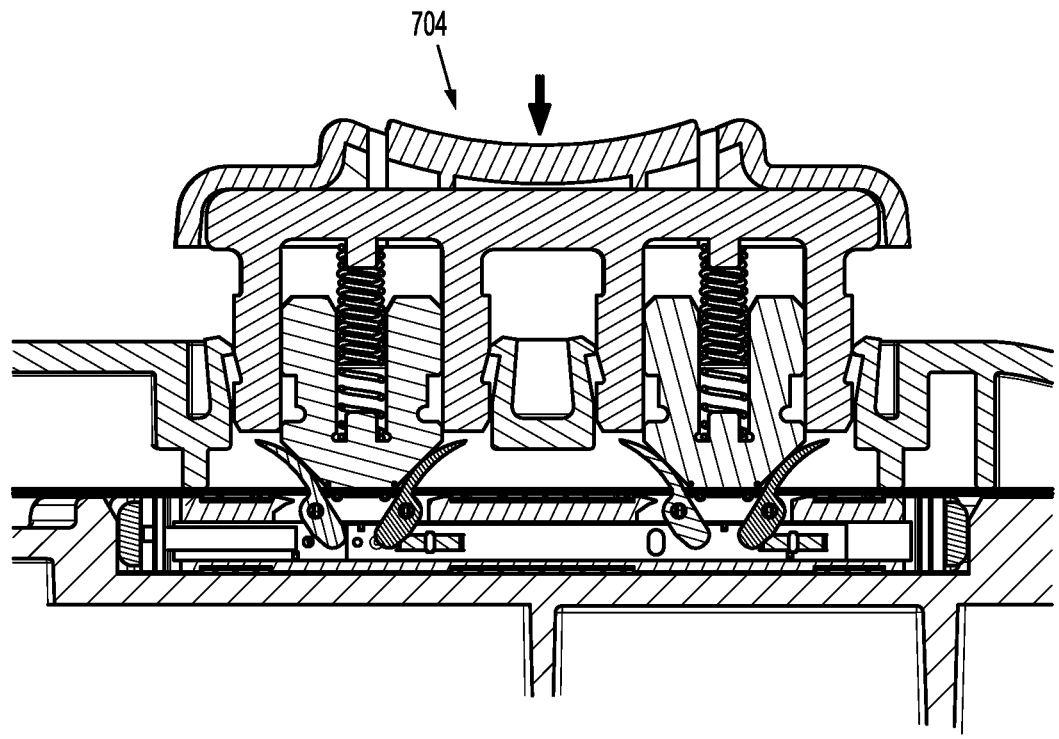
FIG. 22 is an enlarged view of the clip press as shown in FIG. 21, in a second position.
Figure 23:
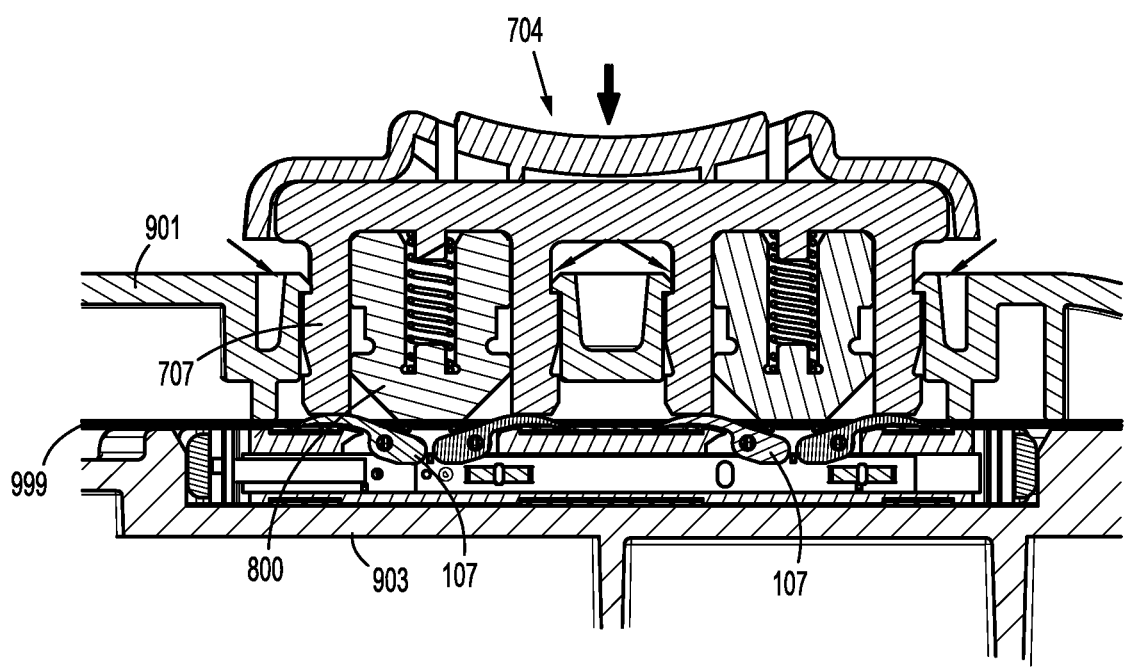
FIG. 23 is an enlarged view of the clip press as shown in FIG. 21, in a third position.

As shown in FIG. 22, when the press surface 803 reaches the implant 999 disposed on the frame arm 104, the chamfered press 800 is prevented from further movement toward the frame arm 104, and the chamfered press 800 moves to the retracted position with further advancement of the clip press 704 against the force of the spring member 713. This allows the body portion 705 to continue moving closer to the frame arm 104 while the chamfered press 804 remains stationary relative to the frame arm 104. By allowing the body portion 705 to move closer to the frame arm 104, the legs 707 complete the closure process and push clips 107 to the closed position, whereas a press with a fixed chamfer would only be able to push the clips 107 partially toward the closed position. Thus, the clip press 704 allows for complete clamping of an implant 999 that is installed on the clips 107.

As shown in FIGS. 24 and 25, implant 999 is shown releasably attached to the implant deployment device 100 wherein the clips 107 are in a closed position.

In some embodiments, a method includes providing a clip press 704 as described above for use with an implant deployment device 100. The method may further include using the clip press 704 to move at least one clip 107 of an implant deployment device 100 from an open position to a closed position. The method may also include using a mesh attachment apparatus 900 to releasably attach a surgical implant to at least one clip of an implant deployment device by compressing the implant 999 onto the at least one clip 107 in an open position and allowing the at least one chamfered surface 801 move the at least one clip from the open position to a closed position.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A surgical system comprising:
    an implant deployment device including at least one frame arm and at least one clip rotatably coupled to the at least one frame arm; and
    a mesh attachment apparatus comprising at least one clip press, the at least one clip press comprising:
        a body portion including at least one recess; and
        at least one chamfered press operably disposed in the at least one recess and configured to move between an extended position protruding at least partially from the at least one recess and a retracted position;
    wherein the mesh attachment apparatus is configured to rotate the at least one clip from an open position to a closed position to facilitate loading an implant onto the implant deployment device, movement of the body portion towards the at least one frame arm urges the at least one clip towards the closed position when the at least one chamfered press is in the retracted position.

2. The system of claim 1, wherein the mesh attachment apparatus further comprises a spring member disposed between the at least one chamfered press and the body portion.

3. The system of claim 2, wherein the spring member biases the at least one chamfered press towards the extended position.

4. The system of claim 1, wherein the at least one chamfered press includes at least one chamfered surface at a distal end of the chamfered press, the at least one chamfered surface defining an angle with respect to a side surface of the chamfered press; and at least one press surface.

5. The system of claim 4, wherein the at least one chamfered surface includes a substantially linear chamfer.

6. A mesh attachment apparatus for use with an implant deployment device, comprising:
    at least one clip press, the at least one clip press comprising:
        a body portion including at least one recess; and
        at least one chamfered press operably disposed in the at least one recess and configured to move between an extended position protruding at least partially from the at least one recess and a retracted position;
    wherein the mesh attachment apparatus is configured to rotate at least one clip coupled to the implant deployment device from an open position to a closed position to facilitate loading an implant onto the implant deployment device, movement of the body portion towards a frame arm of the implant deployment device urges the at least one clip towards the closed position when the at least one chamfered press is in the retracted position.

7. The mesh attachment apparatus of claim 6, wherein the mesh attachment apparatus further comprises a spring member disposed between the at least one chamfered press and the body portion.

8. The mesh attachment apparatus of claim 7, wherein the spring member biases the at least one chamfered press towards the extended position.

9. The mesh attachment apparatus of claim 6, wherein the at least one chamfered press includes at least one chamfered surface at a distal end of the chamfered press, the at least one chamfered surface defining an angle with respect to a side surface of the chamfered press; and at least one press surface.

10. The mesh attachment apparatus of claim 9, wherein the at least one chamfered surface includes a substantially linear chamfer.

11. A method, comprising:
    providing a mesh attachment apparatus for use with an implant deployment device, comprising:
        at least one clip press, the at least one clip press comprising:
            a body portion including at least one recess; and
            at least one chamfered press operably disposed in the at least one recess and configured to move between an extended position protruding at least partially from the at least one recess and a retracted position;
        wherein the mesh attachment apparatus is configured to rotate at least one clip coupled to the implant deployment device from an open position to a closed position to facilitate loading an implant onto the implant deployment device, movement of the body portion towards a frame arm of the implant deployment device urges the at least one clip towards the closed position when the at least one chamfered press is in the retracted position; and
    using the mesh attachment apparatus to rotate the at least one clip of the implant deployment device from the open position to the closed position.

12. The method of claim 11, wherein the mesh attachment apparatus further comprises a spring member disposed between the at least one chamfered press and said body portion, the spring member biasing the at least one chamfered press towards the extended position.

13. The method of claim 11, wherein the at least one chamfered press includes at least one chamfered surface at a distal end of the chamfered press, the at least one chamfered surface defining an angle with respect to a side surface of the chamfered press; and at least one press surface.

14. The method of claim 13, wherein the at least one chamfered surface includes a substantially linear chamfer.

15. The method of claim 11, further comprising using the mesh attachment apparatus to releasably attach the implant to the at least one clip of the implant deployment device by compressing the implant onto the at least one clip in an open position and allowing the at least one chamfered surface rotate the at least one clip from the open position to the closed position.

* * * * *